(12) United States Patent
Houghton et al.

(10) Patent No.: US 11,174,044 B2
(45) Date of Patent: Nov. 16, 2021

(54) ICE ACCRETION APPARATUS

(71) Applicant: GKN Aerospace Services Limited, East Cowes (GB)

(72) Inventors: Steven Mark Houghton, East Cowes (GB); Susanna Halls, East Cowes (GB)

(73) Assignee: GKN Aerospace Services Limited, Isle of Wight (GB)

( * ) Notice: Subject to any disclaimer, the term of this patent is extended or adjusted under 35 U.S.C. 154(b) by 418 days.

(21) Appl. No.: 16/302,744

(22) PCT Filed: May 19, 2017

(86) PCT No.: PCT/GB2017/051416
§ 371 (c)(1),
(2) Date: Nov. 19, 2018

(87) PCT Pub. No.: WO2017/199051
PCT Pub. Date: Nov. 23, 2017

(65) Prior Publication Data
US 2019/0315496 A1    Oct. 17, 2019

(30) Foreign Application Priority Data
May 20, 2016   (GB) .................................. 1608945.0

(51) Int. Cl.
*B64D 15/20*    (2006.01)
*B64F 5/60*     (2017.01)
(Continued)

(52) U.S. Cl.
CPC ................ *B64F 5/60* (2017.01); *B64D 15/20* (2013.01); *G01N 19/04* (2013.01); *G01N 2033/1873* (2013.01)

(58) Field of Classification Search
CPC ........ B64D 15/12; B64D 15/22; B64D 15/20; B64D 15/00; B64D 45/00;
(Continued)

(56) References Cited

U.S. PATENT DOCUMENTS 3,940,622 A * 2/1976 Stallabrass ............. B64D 15/20
250/338.1
3,996,787 A * 12/1976 Edgington ............. B64D 15/20
73/37.6
(Continued)

FOREIGN PATENT DOCUMENTS

JP    2009121999 A    6/2009
JP    2013190426 A    9/2013
(Continued)

OTHER PUBLICATIONS

Jung, Stefan et al; "Are Superhydrophobic Surfaces Best for Icephobicity?"; Langmuir, vol. 27, No. 6, Feb. 14, 2011, pp. 3059-3066, XP055388257, US; ISSN: 0743-7463, DOI: 10.1021/la104762g Experimental Procedure and Apparatus; figures 2(a), 2(b).
(Continued)

*Primary Examiner* — Andre J Allen
(74) *Attorney, Agent, or Firm* — Bejin Bieneman PLC

(57) ABSTRACT

An ice accretion apparatus comprises a column having a longitudinal axis, a side wall, and a central chamber having top and bottom ends. It also comprises a top unit which closes the top end of the chamber and includes a droplet discharge device for producing water droplets, a bottom unit which closes the bottom end of the chamber and includes a target, and chamber cooling means configured to cool the chamber during a test and thereby to cool the water droplets,
(Continued)

whereby, in use during the test, a layer of accreted ice is built up on the target.

19 Claims, 7 Drawing Sheets

(51) Int. Cl.
 *G01N 19/04* (2006.01)
 *G01N 33/18* (2006.01)

(58) Field of Classification Search
 CPC .... B64D 2033/0233; B64D 2045/0085; B64D 33/02; B64D 15/04; B64D 15/14; B64D 15/16; B64D 41/00; B64D 43/02; B64D 15/166; B64D 2013/0603; B64D 11/04; B64D 13/04; B64D 13/08; B64D 15/02; B64D 15/06; B64D 15/08; B64D 15/10; B64D 15/163; B64D 1/10; B64D 1/22; B64D 2013/0644; B64D 2013/0648; B64D 2027/026; B64D 2033/0286; B64D 2045/007; B64D 2203/00; B64D 27/02; B64D 27/10; B64D 27/14; B64D 27/16; B64D 31/06; B64D 31/14; B64D 33/08; B64D 35/08; B64D 47/02; B64D 47/04; G01W 1/14; G01W 1/00; G01W 1/02; G01W 1/08; G01W 1/10; G01W 1/04; G01W 1/06; G01W 1/12; G01W 1/16; G01W 2001/003; G01W 2001/006; G01W 2203/00; G01P 13/02; G01P 13/025; G01P 13/045; G01P 5/02; G01P 5/165; G01P 13/0006; G01P 13/0013; G01P 13/0066; G01P 13/0093; G01P 5/001; G01P 5/06; G01P 5/14; G01P 5/20; G01P 5/245; G01P 5/26; G01P 13/00; G01P 13/002; G01P 13/006; G01P 5/005; G01P 5/04; G01P 5/07; G01P 5/12; G01P 5/18; G01P 5/24
 USPC .......................................... 73/170.01–170.28
 See application file for complete search history.

(56) References Cited

U.S. PATENT DOCUMENTS

| | | |
|---|---|---|
| 4,458,528 A | 7/1984 | Roper |
| 2005/0238428 A1 | 10/2005 | Tandon |
| 2006/0236778 A1 | 10/2006 | Devilbiss |
| 2017/0369176 A1* | 12/2017 | LoPresto ................ B64D 47/08 |
| 2018/0024270 A1* | 1/2018 | Ray ........................ G01S 7/4802 |
| | | 356/336 |
| 2018/0172576 A1* | 6/2018 | Young .................. G01N 17/002 |
| 2019/0120738 A1* | 4/2019 | Houghton .............. G01N 19/04 |

FOREIGN PATENT DOCUMENTS

| | | |
|---|---|---|
| JP | 2013234785 A | 11/2013 |
| JP | 201628953 A | 3/2016 |

OTHER PUBLICATIONS

Yeong, Yong Han et al; "Atmospheric Ice Adhesion on Water-Repellent Coatings: Wetting and Surface Topology Effects"; Langmuir, vol. 31, No. 48; Nov. 13, 2015, pp. 13107-13116, XP055388171, US: ISSN: 0743-7463, DOI: 10.1021/acs.langmuir.5b027252.B. Experimental Setup; figure 1.

Yang, Guomin et al; "Freezing mechanism of supercooled water droplet impinging on metal surfaces"; International Journal of Refrigeration, Elsevier, Paris, FR, vol. 34, No. 8, Jul. 6, 2011, pp. 2007-2017, XP028106816; ISSN: 0140-7007; DOI: 10.1016/J. IJREFRIG.2011.07.001 [retrieved on Jul. 12, 2011] 2. Experimental method; figure 1.

International Search Report and Written Opinion for PCT/GB2017/051416 dated Sep. 22, 2017 (20 pages).

JPO Notification of Reasons for Rejection for Patent Application No. JP2018560824 dated Feb. 16, 2021 (14 pages; with English translation).

China National Intellectual Property Administration Notification of First Office Action for Application No. CN201780031162.3 dated Feb. 22, 2021 (23 pages; with English translation).

Korean Patent Office Notice of Preliminary Rejection for application No. KR10-2018-7036977 dated Mar. 22, 2021 (18 pages; with English machine translation).

* cited by examiner

ICE ACCRETION APPARATUS

CROSS-REFERENCE TO RELATED APPLICATIONS

This application is a national stage of, and claims priority to, Patent Cooperation Treaty Application No. PCT/GB2017/051416, filed on May 19, 2017, which application claims priority to Great Britain Application No. GB1608945.0, filed on May 20, 2016, which applications are hereby incorporated herein by reference in their entireties.

BACKGROUND

When water droplets freeze on a structure, such as an aircraft structure, the effects can be problematic. The formation of ice on an aircraft structure can, for example, change the structure's aerodynamic properties and increase its weight. If ice that has grown on a structure breaks off, this can cause mechanical damage to the structure or to surrounding structures.

It is therefore desirable to develop effective coatings to prevent or reduce the formation of ice on such structures. These coatings are known as "ice-phobic" coatings. They can be usefully applied to structures such as the leading edge of an aircraft wing, to engine blades, the rotor blades of a helicopter, or wind turbine blades.

When ice-phobic coatings are being developed, a new coating must be assessed to determine whether it is, in fact, suitably ice-phobic, prior to developing it further or applying it to a structure. Current methods of testing the effectiveness of potentially ice-phobic coatings are, however, unsatisfactory.

Typically, the performance of a coating is first tested using a bench-top ice adhesion test method. Such methods can provide some data on the adhesion of ice to the coating. The results are not, however, representative of the real-world performance of the coating. This is, in particular, due to the ice created using such methods not being representative of the ice formed in the real-world applications for which the coating is intended.

As a result of this inadequacy of current bench-top ice adhesion methods, ice-phobic coatings may undergo further testing, only to prove unsatisfactory. This unnecessary further testing wastes time and money.

An example of a further testing method is the testing of a sample in an icing wind tunnel, otherwise known as an icing tunnel. This involves placing a sample with a potentially ice-phobic coating in a stream of cooled air and water droplets in a wind tunnel. The process is, however, time-consuming and expensive and requires a relatively large sample to be tested. These are particular disadvantages if the coating being tested proves not to have satisfactory ice-phobic properties and thus not to be suitable for use as an ice-phobic coating.

SUMMARY

This disclosure relates to an ice accretion apparatus including a bench-top ice testing device.

According to a first example, there is provided ice accretion apparatus comprising: a column having a longitudinal axis, a side wall, and a central chamber having top and bottom ends; a top unit which closes the top end of the chamber and includes a droplet discharge device for producing water droplets; a bottom unit which closes the bottom end of the chamber and includes a target; and chamber cooling means configured to cool the chamber during a test and thereby to cool the water droplets, whereby, in use during the test, a layer of accreted ice is built up on the target.

Since the apparatus comprises a droplet discharge device, a chamber cooling means for cooling the chamber during a test, and a target at the bottom of the chamber, the apparatus is self-contained. That is, the apparatus provides, in a single unit, elements for producing water droplets and cooling the chamber through which the spray of water droplets falls, and a target on which the cooled droplets land. It can thus be sized to be a bench-top apparatus and so can be much smaller than an icing wind tunnel. It therefore allows for less expensive and time-consuming testing of a sample than icing wind tunnel testing.

The ice accretion apparatus can be used to build up ice on the target in a manner representative of the way in which ice builds up on a structure in the atmosphere. Atmospheric ice is formed by cooled or super-cooled water droplets freezing on contact with a structure. The ice thus formed is also known as "accreted ice", since it is formed by many droplets. The chamber cooling means for cooling the chamber during a test can be used to create conditions within the apparatus that are representative of atmospheric icing conditions, and therefore create ice that is very similar to atmospheric ice.

The chamber cooling means, in being configured to cool the chamber during the test, may be configured to cool or super-cool the water droplets as they travel down the chamber from the droplet discharge device to the target.

Temperature-Control Means

The ice accretion apparatus may comprise temperature-control means for controlling the temperature of the water supplied to the droplet discharge device.

The temperature-control means may comprise at least one heater. The temperature-control means may comprise a water reservoir heater. The water reservoir heater may be arranged to heat the water supplied to the droplet discharge device. The water reservoir heater may be arranged to heat water in a water reservoir. The temperature-control means may comprise a water supply line heater. The water supply line heater may be arranged to heat water in a water supply line.

When the temperature-control means comprises at least one heater, the temperature-control means can be used to heat the water supplied to the droplet discharge device. This prevents the water supplied to the droplet discharge device from freezing in contact with any part of the droplet discharge device within the cooled chamber. It thus allows water droplets to be produced by the droplet discharge device and then to be cooled in the chamber by the chamber cooling means for cooling the chamber during a test, providing precise control over the temperature of the droplets when they arrive at the target, including the ability to choose different temperatures for the droplets. The temperature-control means and the chamber cooling means therefore provide for simulation of different atmospheric icing conditions, including the formation of glaze ice, rime ice or ice crystals.

Droplet Discharge Device

The droplet discharge device may be arranged to produce a spray of water droplets. The droplet discharge device may be arranged to produce a mist of water droplets. The droplet discharge device may be arranged to produce a pressurised spray of water droplets. The droplet discharge device may be a piezoelectric device. The droplet discharge device may comprise at least one piezoelectric actuator. The at least one piezoelectric actuator may be arranged, when an electric current is applied to the actuator, to drive water from the device.

The droplet discharge device may comprise at least one nozzle for forming a water droplet. The nozzle may have a nozzle diameter that at least partially determines a diameter of a water droplet formed by the nozzle. The droplet discharge device may be arranged to have an adjustable nozzle diameter for adjusting a diameter of a water droplet formed by the nozzle.

Pressurising Means

The apparatus may comprise pressurising means for pressurising water supplied to the droplet discharge device. The apparatus may comprise pressurising means for controlling the pressure of water supplied to the droplet discharge device. The pressurising means may be a pump. The pump may be arranged to pump water.

When the apparatus comprises pressurising means for pressurising water supplied to the droplet discharge device, water droplets produced by the droplet discharge device fall faster than they would under gravity alone. This provides a more accurate simulation of atmospheric conditions, for example conditions in which an object moves into water droplets, or in which water droplets are driven by the wind.

When the apparatus comprises pressurising means for controlling the pressure of the water supplied to the droplet discharge device, this allows the pressure at which the water droplets are produced by the droplet discharge device to be controlled. This helps to determine the speed with which the water droplets fall and at which they reach the target, again allowing the apparatus to be used to more accurately simulate any of a variety of atmospheric conditions. The pressurising means for controlling the pressure of the water supplied to the droplet discharge device can also be used to determine the size of the water droplets produced by the droplet discharge device. Specifically, it can be used to increase the pressure of the water supplied to the droplet discharge device and thereby to decrease the size (diameter) of the water droplets produced by the droplet discharge device. In general, the greater the increase in pressure, the smaller the diameter of the water droplets produced by the droplet discharge device.

When a pump arranged to pump water is used to control the pressure of the water supplied to the droplet discharge device, no gas needs to be used to pressurise the water. This means that no gas need be added to the chamber via the droplet discharge device. Thus, the volume of gas in the chamber can be controlled, for example to more accurately represent high-altitude atmospheric conditions, or to reduce nucleation points for the formation of ice within the chamber.

Water Droplet Generation System

The apparatus may comprise a water reservoir for storing water to be supplied to the droplet discharge device. The apparatus may comprise a water supply line for supplying water to the droplet discharge device. The apparatus may comprise a water temperature controller. When the temperature-control means comprises at least one heater, the water temperature controller may be arranged to control the at least one heater. When the apparatus comprises pressurising means, the apparatus may further comprise a water pressure controller. The apparatus may comprise a water pressure and temperature controller.

The apparatus may comprise a water droplet generation system. The water droplet generation system may comprise the temperature-control means. The water droplet generation system may comprise the water reservoir. The water droplet generation system may comprise the water supply line. The water droplet generation system may comprise the water temperature controller. The water droplet generation system may comprise the droplet discharge device. The water droplet generation system may comprise the pressurising means. The water droplet generation system may comprise the water pressure controller. The water droplet generation system may comprise the water pressure and temperature controller.

Segments

The side wall may be annular in cross-section. The side wall may be substantially tubular in shape. The side wall may comprise a plurality of tubular segments. The tubular segments may be releasably stacked on top of one another. The side wall may comprise a material between the tubular segments that is less thermally conductive than a material from which the tubular segments are formed. In this way, the tubular segments can be thermally insulated from one another. This can help to preserve a temperature gradient created within the chamber (discussed further below).

When the side wall comprises a plurality of tubular segments, the number of tubular segments can be varied to alter the separation height between the droplet discharge device and the target, and thus vary the speed of impact of the droplets on the target.

Chamber Cooling Means

The chamber cooling means may be configured to produce a temperature profile between the top and bottom ends of the chamber. The chamber cooling means may be configured to produce a temperature gradient between the top and bottom ends of the chamber. The chamber cooling means may be configured to cool the bottom end of the chamber to a lower temperature than the top end.

The chamber cooling means may comprise at least one wall cavity in the side wall and an inlet and an outlet for passing a cooling fluid through the at least one cavity. When the side wall of the column comprises a plurality of tubular segments, each tubular segment may define one wall cavity. Each tubular segment may comprise an inlet and an outlet for passing a cooling fluid through the cavity.

The above arrangements allow for the flow rate of cooling fluid through one segment to differ from the flow rate of cooling fluid through another segment. This can be achieved by controlling the flow rate of cooling fluid through each segment individually. In this way, a temperature gradient within the chamber can be created and can be varied. For example, the top of the column may be kept at one temperature and the bottom of the column may be kept at another temperature, with a temperature gradient between. This gives control over icing conditions within the chamber and the kind of ice accreted on the target.

Chamber Heating Means

The ice accretion apparatus may comprise chamber heating means for heating the chamber between tests.

The chamber heating means may comprise at least one heater jacket around the column. When the column comprises a plurality of tubular segments, the or each heater jacket may be around at least one of the plurality of tubular segments of the column. There may be a plurality of heater jackets, each around a tubular segment of the column. There may be a heater jacket around each of the plurality of tubular segments of the column.

The chamber heating means, for example in the form of a heater jacket, enables the chamber to be dried out after a test. This allows for the more accurate creation in a subsequent test of icing conditions representative of atmospheric icing conditions.

The chamber heating means also allows for the apparatus to be handled after a test since it can be used to heat the chamber to a temperature at which a user handling the apparatus would not suffer frostbite or cryogenic burns. Relative to an apparatus without chamber heating means, the chamber heating means therefore make the apparatus safer to use.

The chamber heating means also provides for further control of the temperature inside the column during a test. In particular, when the chamber heating means comprises at least one heater jacket around at least one of the plurality of tubular segments of the column, the chamber heating means enables the temperature profile inside the chamber to be controlled.

For example, in embodiments in which the chamber heating means comprises a single heater jacket around one of the tubular segments of the column, this jacket may be heated while the remaining tubular segments are cooled such that the portion of the chamber defined by the tubular segment with the heater jacket is warmer than the remainder of the chamber.

In embodiments in which the chamber heating means comprises a plurality of heater jackets, each around a tubular segment of the column, at least one of the plurality of heater jackets can be heated to a temperature that is different from the remainder of the heater jackets, such that the portions of the chamber defined by different tubular segments of the column are at different temperatures. In this way, the top of the column may be kept at one temperature, for example room temperature, and the bottom of the column may be kept at another temperature, for example −20° C., with a temperature gradient between. This gives further control over icing conditions within the chamber and the kind of ice accreted on the target.

Insulated Jacket

The apparatus may comprise an insulated jacket around the column. When the column comprises a plurality of tubular segments, the apparatus may comprise an insulated jacket around at least one of the plurality of tubular segments of the column. The apparatus may comprise a plurality of insulated jackets, each around a tubular segment of the column. The apparatus may comprise an insulated jacket around each of the plurality of tubular segments of the column. The or each insulated jacket may be around a heater jacket.

The or each insulated jacket provides for more accurate temperature control within the chamber, since inside of the chamber is thermally insulated from the environment. The or each insulated jacket can also reduce heating of the chamber cooling means and thereby provide for more efficient cooling of the chamber. When the or each insulated jacket is around a heater jacket, the or each insulated jacket reduces heat loss from the heater jacket, increasing the efficiency of the chamber heating means.

Valve Means

The apparatus may comprise valve means for introducing a volume of fluid into the chamber and for sealing the volume of fluid in the chamber. The fluid may be a gas.

The valve means provides for yet more accurate simulation in the chamber of a variety of atmospheric conditions, since it allows the volume and type of fluid or gas allowed into and retained within the chamber to be controlled.

Pumping Means

The apparatus may comprise pumping means for producing a reduced pressure in the chamber.

The provision of pumping means for producing a reduced pressure in the chamber is in contrast to many icing wind tunnels, in which pressure generally cannot be controlled.

The pumping means allows the volume of air within the system to be reduced. This provides for a more realistic simulation of real-world icing conditions. For example, if the pumping means is used to create a vacuum within the system, nucleation points for the cooled or super-cooled droplets are eliminated or at least reduced, which prevents ice crystals from forming, and ensures that the sample is frost-free.

The pumping means can also be used to reduce moisture in the chamber. This creates a dry atmosphere, which again may provide a more realistic simulation of real-world icing conditions.

Sensors and Controller

The apparatus may comprise at least one temperature sensor for measuring the temperature inside the chamber. The at least one temperature sensor may be arranged to supply output signals to at least one controller. The apparatus may comprise at least one pressure sensor for measuring the pressure inside the chamber. The at least one pressure sensor may be arranged to supply output signals to at least one controller. The apparatus may comprise the at least one controller. The at least one controller may be arranged to control the valve means and/or pumping means to control the pressure inside the chamber. The at least one controller may be arranged to control the valve means and/or pumping means to control the pressure inside the chamber based on output signals supplied by the at least one pressure sensor. The at least one controller may be arranged to control the chamber cooling means and/or chamber heating means to control the temperature inside the chamber. The at least one controller may be arranged to control the chamber cooling means and/or chamber heating means to control the temperature inside the chamber based on output signals supplied by the at least one temperature sensor.

The at least one temperature and/or pressure sensor allow for the accurate simulation of a variety of atmospheric conditions since they can be used to provide feedback to the at least one controller on the temperature and/or pressure within the chamber, which can in turn control the temperature and/or pressure within the chamber.

Releasable Fitting

The droplet discharge device may be releasably fitted to the top unit of the apparatus. The column may be releasably fitted to the bottom unit of the apparatus.

When the droplet discharge device is releasably fitted to the top unit of the apparatus, the droplet discharge device can be changed between tests. For example, a first droplet discharge device with a nozzle of a first diameter may be used for one test, giving a first size of droplet, and a second droplet discharge device with a nozzle of a second diameter may be used for another test, giving a second size of droplet. In this way, the size of the droplets can be varied between tests. This allows for a greater range of icing conditions to be simulated, making the apparatus more versatile.

When the column is releasably fitted to the bottom unit of the apparatus, the bottom unit, including the target, can be changed between tests. This allows the apparatus to be used for a greater range of icing tests than if the bottom unit were not releasably fitted to the column.

Viewing Port

The apparatus may comprise a viewing port arranged to allow observation from outside the apparatus of the target.

Certain tests that can be run using the apparatus provide more accurate results if a sample undergoing the test can be viewed during the test. For example, if a sample is being tested to determine how strongly ice adheres to the sample, it is useful for a user to be able to see how much ice has accumulated on the sample before it is tested, and then at what point the ice separates from the sample. The viewing port allows for such observation.

Second Aspect

According to a second example, there is provided ice formation apparatus comprising: a column having an annular wall defining a chamber which has a top end and a bottom end, wherein the annular wall of the column has a wall cavity with an inlet and an outlet for a cooling fluid for cooling the chamber; a droplet discharging device for producing a water droplets at the top end of the chamber; and a target at the bottom end of the chamber on which, in use, a layer of accreted ice is built up from the water droplets.

Optional features of the first aspect are also optional features of the second aspect, with changes of terminology being inferred by the skilled artisan where necessary for these to make sense. For example, when applying optional features of the first aspect to this second aspect, the expression "side wall" would be interpreted as "annular wall", and the expression "ice accretion apparatus" would be interpreted as "ice formation apparatus".

Ice Adhesion Test Device

The ice accretion apparatus may comprise an ice adhesion test device. The bottom unit may be in the form of an ice adhesion test device.

When the ice accretion apparatus comprises an ice adhesion test device, the adhesion of ice to the target may be tested.

Target

The ice adhesion test device may comprise the target. In other words, the target of the ice accretion apparatus may be part of the ice adhesion test device. The target may be in the form of a well, in which, in use, a layer of accreted ice is built up. The target may comprise a sample plate at the bottom of the well and an ice-engagement element positioned circumferentially around the sample plate and providing a side wall of the well. The sample plate may be rotatable relative to the ice-engagement element.

When the ice adhesion test device comprises a target in the form of a well in which, in use, a layer of accreted ice is built up, the apparatus allows the adhesion of accreted ice to a sample to be tested. When the sample has a potentially ice-phobic coating, the ice accretion apparatus can therefore be used to test the properties of the coating in relation to ice which closely approximates atmospheric icing.

Torque Means

The ice adhesion test device may comprise torque means for applying a rotational torque between the sample plate and an ice-engagement element peripherally arranged to try, in use, to rotate the sample plate relative to the ice-engagement element against the resistance of the layer of accreted ice.

The torque means allows for a stress to be applied to the ice, such that, if the coating is ice-phobic, the ice will separate from the sample plate.

Transducer Means

The ice adhesion test device may comprise transducer means for measuring the rotational torque. The ice adhesion test device may comprise transducer means for measuring the stress caused by a rotational torque applied by the torque means when the layer of accreted ice at least partially separates from the sample plate. The ice adhesion test device may comprise transducer means for measuring the rotational torque and for measuring the stress caused by a rotational torque applied by the torque means when the layer of accreted ice at least partially separates from the sample plate.

The transducer means for measuring the rotational torque allows the torque at which the ice separates from the sample plate to be measured, thereby indicating the adhesion of the ice to the sample plate.

Rotatable Sample Plate

The sample plate may be rotatable. The ice-engagement element may be fixed in position. The sample plate may be rotatable relative to the ice-engagement element. The torque means may be arranged to apply a rotational torque to the sample plate.

When the sample plate is rotatable and the ice-engagement element is fixed in position, the transducer means can measure the rotational torque and/or the stress at which the ice separates from the sample plate, which is of interest when the sample plate bears a potentially ice-phobic coating to be tested, rather than the rotational torque at which the ice separates from the ice-engagement element.

Preventing Rotation of Ice Relative to the Ice-Engagement Element

The ice-engagement element may be an annulus. The ice-engagement element may be shaped to prevent rotation of the layer of accreted ice relative to the ice-engagement element. The ice-engagement element may have a non-circular inner peripheral wall. The ice-engagement element may have an inner peripheral wall which has protrusions for keying with the layer of accreted ice to prevent rotation of the layer of accreted ice relative to the ice-engagement element. The ice-engagement element may have an inner peripheral wall which has recesses for keying with the layer of accreted ice to prevent rotation of the layer of accreted ice relative to the ice-engagement element. The inner peripheral wall, when it has protrusions or recesses, may be substantially circular. The ice-engagement element may be mechanically roughened to prevent rotation of the layer of accreted ice relative to the ice-engagement element. The ice-engagement element may have an inner peripheral wall which is mechanically roughened to prevent rotation of the layer of accreted ice relative to the ice-engagement element.

When the ice-engagement element is shaped to prevent rotation of the layer of accreted ice relative to the ice-engagement element, a more accurate measurement can be made of the adhesion of the accreted ice to the sample. This is because the shape of the ice-engagement element ensures that the ice does not simply rotate freely with respect to the ice-engagement element such that there is no stress on the ice. Instead, the ice is held in place by the shape of the ice-engagement element such that the rotation of the sample plate imparts stress to the ice. The transducer means can then measure the rotational torque and/or the stress at which the ice ceases to adhere to the sample plate.

Variable-Diameter Ice-Engagement Element

The ice-engagement element may be arranged to be adjustable in diameter. The ice-engagement element may have an adjustable inner diameter. The ice-engagement element may be arranged to define an area of the sample plate to be exposed to water droplets. The side wall may be arranged to be adjustable in diameter.

In this way, the area to be exposed to the water droplets can be adjusted to allow for different sizes of sample plates.

Runback Ice Test Device

The ice accretion apparatus may comprise a runback ice test device. The bottom unit may be in the form of a runback ice test device.

When the ice accretion apparatus comprises a runback ice test device, runback ice can be simulated and observed.

Runback ice can be defined as ice that forms when existing ice on one part of a surface melts and re-freezes elsewhere. Runback ice can form, for example, aft of a heated leading edge of a wing or tailplane, when water droplets freeze on the leading edge and are then melted by a heating system of the heated leading edge, such that the water runs back and re-freezes. Runback ice can also form on heated propeller blades. In both examples, the above-described problems of increased weight, reduced aerodynamic performance and mechanical damage can occur. It is thus useful to be able to properly simulate and study the formation of runback ice.

Target

The runback ice test device may comprise the target. In other words, the target of the ice accretion apparatus may be part of the runback ice test device. The target may comprise a platform having an upper face which is separated into a first section and a second section by a protruding thermal barrier. The runback ice test device may comprise platform inclination means arranged to incline the platform such that the second section is above the first section.

Heater Means

The runback ice test device may comprise first heater means for producing localised heating of the first section of the platform. The first heater means may be for keeping the first section of the platform substantially free of accreted ice as a layer of accreted ice is, in use, built up on the second section of the platform. The runback ice test device may comprise second heater means for producing localised heating of the second section of the platform. The second heater means may be for producing runback of melted ice from the layer of accreted ice over the barrier and onto the first section of the platform when the platform is inclined.

The runback ice test device provides for a simulation of runback ice. The formation of runback ice differs from the formation of accreted ice in that runback ice in a particular location is, as discussed above, formed by ice from elsewhere melting and reforming at the location.

By providing first heater means for producing localised heating of the first section of the platform for keeping the first section of the platform substantially free of accreted ice as a layer of accreted ice is, in use, built up on the second section of the platform, the runback ice test device can keep the section of the platform that is lower when the platform is inclined free of ice so that the creation of runback ice on the lower section can be studied.

By providing second heater means for producing localised heating of the second section of the platform for producing runback of melted ice from the layer of accreted ice and over the barrier and onto the first section of the platform, the runback ice test device can melt the accreted ice so that it runs onto the first section of the platform, where it may then re-freeze, creating runback ice.

Controller

The runback ice test device may comprise a heater means controller. The heater means controller may be for independently switching on and off the first and second heater means.

The heater means controller for independently switching on and off the first and second heater means allows the first heater means to be switched on while the second heater means is switched off, thereby providing a mode in which the first section (which is lower when the platform is inclined) is heated to be kept clear of ice and the second section (which is higher when the platform is inclined) is not heated such that ice can be accreted on the second section. It also allows the first heater means to be switched off while the second heater means is switched on, thereby providing a mode in which the second section is heated to melt accreted ice, and the first section is not heated, to allow runback ice to form on the first section.

The heater means controller may be for controlling the temperature to which the first and second heater means are heated.

This can allow for a more efficient use of energy (relative to a device in which the temperatures cannot be controlled or are fixed), since if desired, the first heater means can be heated to the minimum temperature at which the first section can still be kept clear of ice, taking into account the temperature within the chamber. This uses less energy than if the first heater means were heated to a higher temperature.

The heater means controller for controlling the temperature to which the first and second heater means are heated also allows for the simulation of a wider variety of runback icing conditions than with devices in which the temperatures are fixed.

Adjusting the Angle of Inclination

The platform inclination means may be arranged to adjust the angle of inclination of the platform of the target.

When the platform inclination means is arranged to adjust the angle of inclination of the platform of the target, the runback ice test device can be used to simulate the formation of runback ice on a variety of different structures or at different angles of inclination of those structures. For example, the angle between a heated portion of a wing and a portion of a wing on which ice runback may occur may be different from the angle between a heated portion of a tailplane and a portion of the tailplane on which ice runback may occur. The means for adjusting the angle of inclination of the platform of the target allows the same runback ice test device to test ice runback at either of these angles, thereby simulating ice runback on either of these structures.

Third Aspect: Method

According to a third example, there is provided a method of operating the ice accretion apparatus of the first aspect, the method comprising operating the droplet discharge device to produce water droplets and, with the chamber cooling means, cooling the water droplets, such that a layer of accreted ice is built up on the target.

Order of Cooling

The method may comprise cooling the water droplets as they travel down the chamber from the droplet discharge device to the target. In this way, the water droplets freeze when they hit the target.

The method may comprise cooling the water droplets once they have landed on the target. In this way, the water droplets land as a liquid on the target, and then freeze.

Pulsing

The method may comprise operating, at intervals, the droplet discharge device to produce water droplets. The method may comprise interrupting, at intervals, the production of water droplets by the droplet discharge device.

In this way, rather than generating a substantially continuous flow or spray of water droplets, the production of water droplets can be interrupted. This method can be used to create layers of ice on the target, since the water droplets that have fallen on the target have time to freeze while water droplets are not being produced, and before the production of water droplets is resumed.

Temperature Gradient

The method may comprise creating a temperature gradient within the central chamber of the ice accretion apparatus.

The method may comprise cooling a portion of the chamber proximal the top unit to a temperature above 0° C. and cooling a portion of the chamber proximal the bottom unit to a temperature of 0° C. or below. The method may comprise cooling a portion of the chamber proximal the top unit to a temperature above 0° C. and cooling a portion of the chamber proximal the bottom unit to a temperature below 0° C.

The method may comprise cooling a portion of the chamber proximal the top unit to a temperature of at least 0° C. and up to 20° C. The method may comprise cooling a portion of the chamber proximal the top unit to a temperature of at least 0° C. and up to 15° C. The method may comprise cooling a portion of the chamber proximal the top unit to a temperature of at least 0° C. and 10° C.

In this way, a portion of the chamber proximal the top unit can be kept at a temperature at which the droplet discharge device can produce water droplets without freezing.

The method may comprise cooling a portion of the chamber proximal the bottom unit to a temperature between 0° C. and −40° C.

In this way, the portion of the chamber proximal the bottom unit can be kept at a temperature at which the water droplets will freeze on the target to produce a layer of accreted ice.

The method may comprise cooling a portion of the chamber proximal the bottom unit to a temperature between 0° C. and −5° C. In this way, clear ice can be built up on the target. The method may comprise cooling a portion of the chamber proximal the bottom unit to a temperature between −5° C. and −10° C. In this way, clear ice or mixed ice can be built up on the target. The method may comprise cooling a portion of the chamber proximal the bottom unit to a temperature between −10° C. and −15° C. In this way, mixed or rime ice can be built up on the target. The method may comprise cooling a portion of the chamber proximal the bottom unit to a temperature between −15° C. and −40° C. In this way, rime ice can be built up on the target.

In general, the type of ice (clear, mixed, and rime) that can accrete is dependent on a number of factors including, but not limited to, ambient temperature, temperature of accreting surface, Liquid Water Content (LYC), droplet size, droplet impingement velocity, altitude (pressure), and humidity.

The method may comprise, when the ice accretion apparatus comprises chamber heating means, operating the chamber heating means to heat a portion of the central chamber so as to create a temperature gradient within the chamber. The method may comprise operating the chamber heating means to heat a portion of the chamber proximal to the top unit.

When the chamber heating means comprises at least one heater jacket around the column, the method may comprise operating the at least one heater jacket to heat a portion of the central chamber so as to create a temperature gradient within the chamber. The method may comprise operating a heater jacket around a portion of the central chamber proximal the top unit of the apparatus so as to heat the portion of the chamber proximal the top unit. The method may comprise operating a first heater jacket to heat a first portion of the central chamber and operating a second heater jacket to heat a second portion of the central chamber, the method comprising heating the second heater jacket to a higher temperature than the first heater jacket so as to heat the second portion of the chamber to a higher temperature than the first portion of the chamber. The second heater jacket may be around a portion of the central chamber proximal the top unit of the apparatus.

The method may comprise, when the chamber cooling means comprises a plurality of tubular segments, each tubular segment defining a wall cavity and each tubular segment comprising an inlet and an outlet for passing a cooling fluid through the respective wall cavity, creating a temperature gradient within the central chamber of the ice accretion apparatus by passing a cooling fluid through the wall cavity of a first one of the tubular segments and passing a cooling fluid through the wall cavity of a second one of the tubular segments at a lower volumetric flow rate than the volumetric flow rate at which the cooling fluid is passed through the wall cavity of the first one of the tubular segments, so as to cool the portion of the central chamber defined by the first one of the tubular segments to a lower temperature than the portion of the central chamber defined by the second one of the tubular segments.

The method may comprise, when the chamber cooling means comprises a plurality of tubular segments, each tubular segment defining a wall cavity and each tubular segment comprising an inlet and an outlet for passing a cooling fluid through the respective wall cavity, creating a temperature gradient within the central chamber of the ice accretion apparatus by passing a first cooling fluid through the wall cavity of a first one of the tubular segments and passing a second cooling fluid through the wall cavity of a second one of the tubular segments, the first cooling fluid at a lower temperature than the second cooling fluid, so as to cool the portion of the central chamber defined by the first one of the tubular segments to a lower temperature than the portion of the central chamber defined by the second one of the tubular segments.

The method may comprise, when the chamber cooling means comprises a plurality of tubular segments, each tubular segment defining a wall cavity and each tubular segment comprising an inlet and an outlet for passing a cooling fluid through the respective wall cavity, creating a temperature gradient within the central chamber of the ice accretion apparatus by passing a cooling fluid through the wall cavity of a first one of the tubular segments and then passing the cooling fluid through the wall cavity of a second one of the tubular segments, so as to cool the portion of the central chamber defined by the first one of the tubular segments to a lower temperature than the portion of the central chamber defined by the second one of the tubular segments.

The first one of the tubular segments may be a tubular segment proximal to the bottom unit. In this way, a temperature gradient is created in which the bottom of the chamber (nearest the target) is cooler than the top of the chamber (nearest the droplet discharge device).

Droplet Size

When the ice accretion apparatus comprises pressurising means for controlling the pressure of the water supplied to the droplet discharge device, the method may comprise controlling the pressure of the water supplied to the droplet discharge device to control a diameter of the water droplets produced by the droplet discharge device.

The method may comprise increasing the pressure of the water supplied to the droplet discharge device to decrease the diameter of the water droplets produced by the droplet discharge device.

When the droplet discharge device is a piezoelectric device, the method may comprise controlling a current supplied to piezoelectric elements of the piezoelectric device, so as to control the diameter of water droplets produced by the piezoelectric device.

Fourth Aspect: System

According to a fourth example, there is provided an ice accretion system comprising: a column having a longitudinal axis, a side wall, and a central chamber having top and bottom ends; a top unit which closes the top end of the chamber and is arranged to receive a droplet discharge device for producing water droplets; a first droplet discharge device arranged to be fitted to the top unit and comprising at least one nozzle having a first diameter that at least partially determines a diameter of at least one water droplet formed by the at least one nozzle having the first diameter; a second droplet discharge device arranged to be fitted to the top unit and comprising at least one nozzle having a second diameter that at least partially determines a diameter of at least one water droplet formed by the at least one nozzle having the second diameter, the second diameter different from the first diameter; a bottom unit which closes the bottom end of the chamber and includes a target; and chamber cooling means configured to cool the chamber during a test and thereby to cool droplets produced by the first or second droplet discharge device, whereby, in use during the test, a layer of accreted ice is built up on the target.

By providing a first droplet discharge device arranged to be fitted to the top unit and comprising at least one nozzle having a first diameter that at least partially determines a diameter of at least one water droplet formed by the at least one nozzle having the first diameter, and a second droplet discharge device arranged to be fitted to the top unit and comprising at least one nozzle having a second diameter that at least partially determines a diameter of at least one water droplet formed by the at least one nozzle having the second diameter, the second diameter different from the first diameter, the system allows for the first and second droplet discharge devices to be interchanged to produce water droplets of different diameters.

Optional features of the first aspect and second aspects are also optional features of the fourth aspect, with changes of terminology being inferred by the skilled artisan where necessary for these to make sense.

BRIEF DESCRIPTION OF THE DRAWINGS

Specific embodiments will be described below by way of example only and with reference to the accompanying drawings, in which.

DESCRIPTION OF CERTAIN EXAMPLE EMBODIMENTS

Overview

Figure 1:
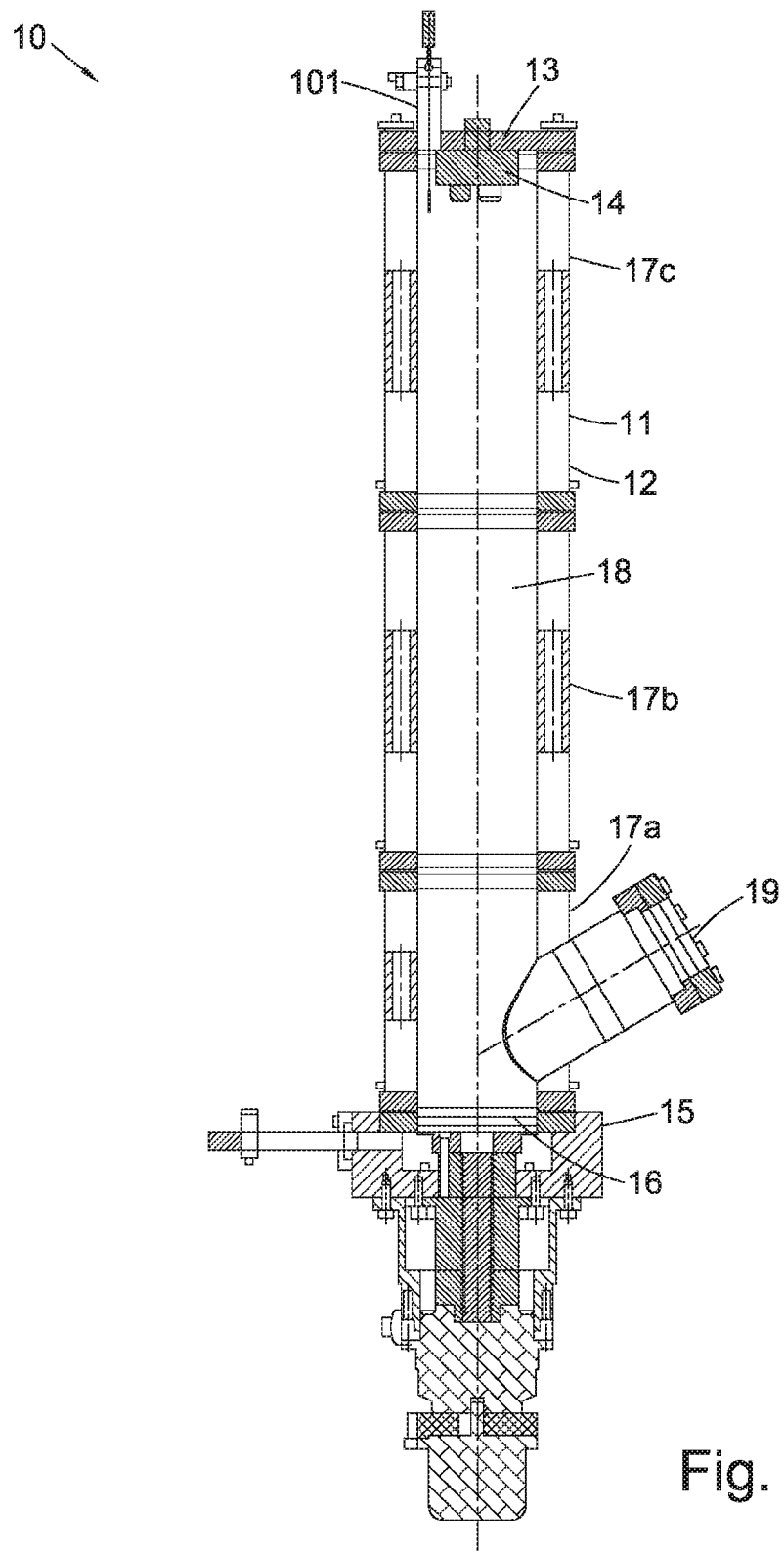
FIG. 1 shows a cross-sectional view of an ice accretion apparatus in the form of a bench-top icing device.

FIG. 1 shows an ice accretion apparatus in the form of a bench-top icing device 10. In overview, the bench-top icing device 10 (hereinafter, the "icing device") is shaped as a column 11. The column 11 is defined by a side wall 12 (hereinafter, a "wall"), which in this embodiment is annular in shape. The wall 12 is formed of three tubular segments in the form of wall sections: a first wall section 17a, a second wall section 17b, and a third wall section 17c. The second wall section 17b is stacked on top of the first wall section 17a. The third wall section 17c is stacked on top of the second wall section 17b. In other embodiments, there may be more or fewer tubular segments. In this embodiment, each wall section 17a, 17b, 17c is substantially circular in cross-section. Thus, the wall 12 of the column 11 forms a tube that is substantially circular in cross-section. The wall 12 defines a central chamber 18 (hereinafter a "chamber") within it. This chamber 18 is therefore also substantially circular in cross-section.

At the top end of the chamber 18 there is a droplet discharge device in the form of a nozzle device 14. This nozzle device 14 is part of a top unit in the form of droplet discharge device holder 13. The droplet discharge device holder 13 acts as a lid on the top of the column 11, closing the chamber 18. The droplet discharge device holder 13 is releasably fitted to the third wall section 17c. The nozzle device 14 forms part of a water droplet generation system (not shown in FIG. 1).

At the bottom end of the chamber 18, there is a target. The target is part of a bottom unit which is, in this embodiment, an ice adhesion test device 15. In this embodiment, the target is in the form of a well 16 of the ice adhesion test device 15. The ice adhesion test device 15 is releasably fitted to the first wall section 17a.

The first wall section 17a also has a viewing port 19. The viewing port 19 in the first wall section 17a allows for observation of a sample (not shown) within the well 16.

Water Droplet Generation System

Figure 2:
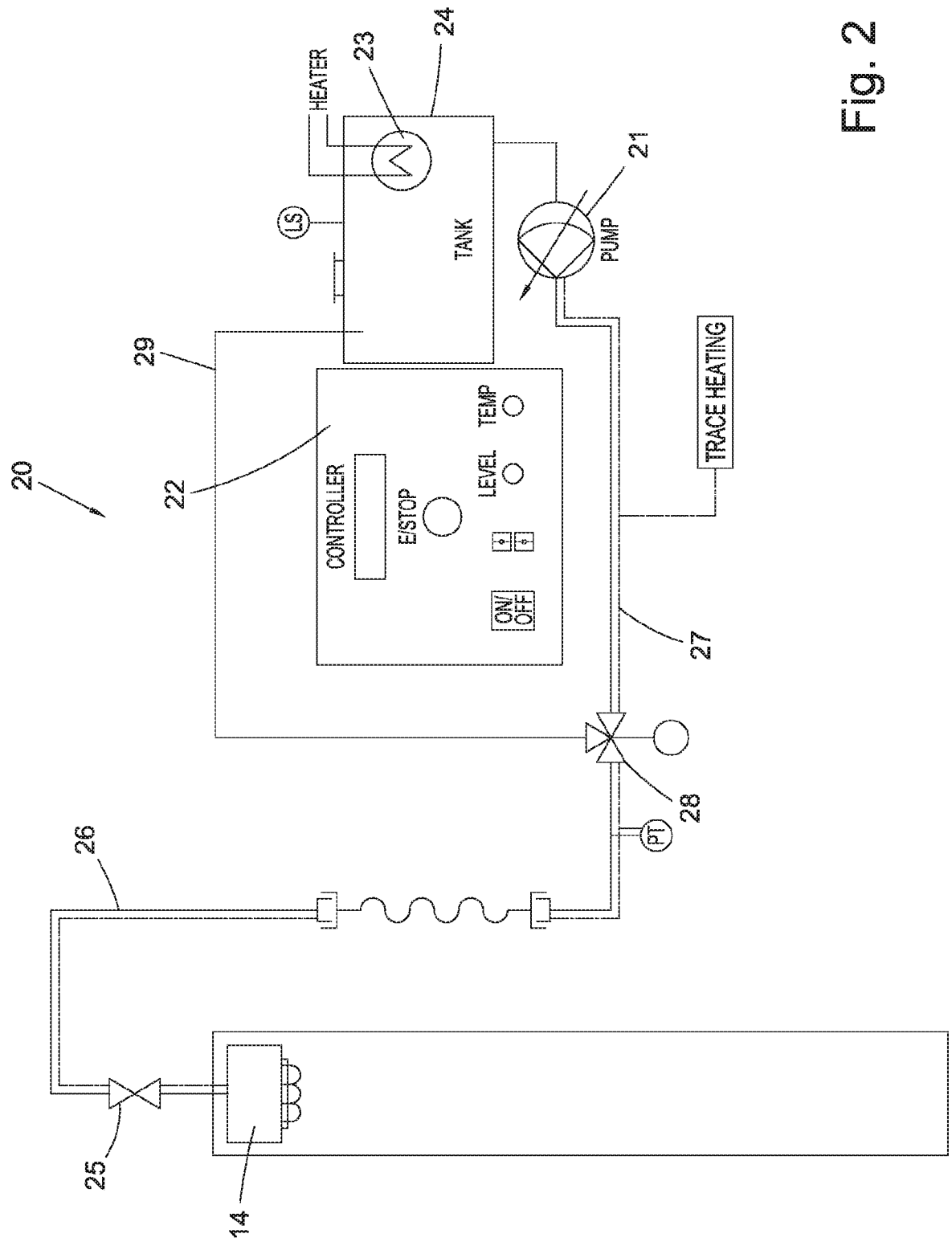
FIG. 2 shows, schematically, a water droplet generation system.
Figure 3A:
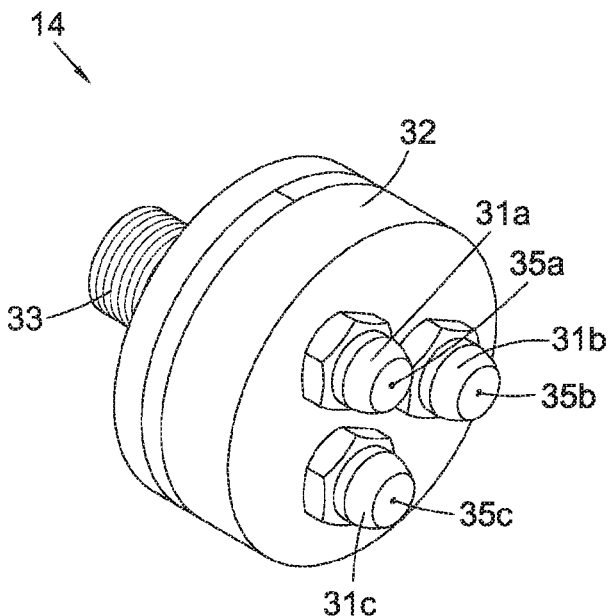
FIG. 3a shows a perspective view of a droplet discharge device.
Figure 3B:
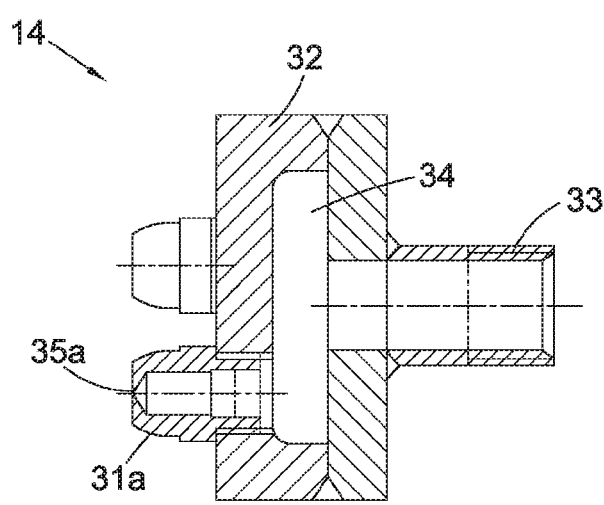
FIG. 3b shows a cross-sectional view of a droplet discharge device.

With reference to FIGS. 2, 3a and 3b, the nozzle device 14 and the water droplet generation system 20 of which it forms part will now be described in more detail. In overview, and with particular reference to FIG. 2, the water droplet generation system 20 comprises the nozzle device 14 in the droplet discharge device holder 13 (not shown in this figure), a water reservoir in the form of a tank 24 and a water supply line 26 that connects the nozzle device 14 to the tank 24. The water droplet generation system 20 also comprises a water reservoir heater in the form of a tank heater 23 in the tank 24, and a water supply line heater in the form of a trace heater 27, as well as a water pressure and temperature controller 22 that controls the tank heater 23, trace heater 27 and pressurising means in the form of a pump 21. Finally, the water droplet generation system 20 comprises, on water the supply line 26, the pump 21, a pressure-reducing valve 28 connected to a bleed line 29 that is also connected to the tank 24, and a gate valve 25.

With continued reference to FIG. 2, the configuration of these components will now be described in more detail. The tank 24 is connected to two lines: the water supply line 26, and the bleed line 29. The water supply line 26 is connected at one end to the tank 24, and at the other end to the nozzle device 14. The bleed line 29 is connected at one end to the tank 24, and at the other end to the water supply line 26. The tank heater 23 is located within the tank 24, to heat water in the tank 24.

Starting at the end of the water supply line 26 that is connected to the tank 24, the configuration of the water supply line 26 will now be described. Between the tank 24 and the nozzle device 14 the water supply line 26 is connected to the pump 21. The pump 21 is arranged so that it can draw water from the tank 24 into the water supply line 26 and thus increase the water pressure in the water supply line 26. Beyond the pump 21 (i.e. on the water supply line 26 and on the other side of the pump 21 from the tank 24), the water supply line 26 is connected to a trace heater 27. The trace heater 27 is arranged to further heat water within the water supply line 26. Between the pump 21 and the nozzle device 14, the water supply line 26 is also connected to a pressure-reducing valve 28. The pressure-reducing valve 28 is a three-way valve that is configured to allow water through the water supply line 26 from the tank 24 towards the nozzle device 14 and from the water supply line 26 (either from the tank 24 side of the pressure-reducing valve 28 or from the nozzle device 14 side of the pressure-reducing valve 28) into the bleed line 29. This serves to reduce water pressure in the water supply line 26 if necessary. The bleed line 29 is connected to the tank 24 so that it can return water bled from the water supply line 26 into the tank 24. Between the pressure-reducing valve 28 and the nozzle device 14, the water supply line 26 is still connected to the trace heater 27. The water supply line 26 is also connected to the gate valve 25. The gate valve 25 is arranged to stop or allow the flow of water through the water supply line 26 from the tank 24 to the nozzle device 14.

As mentioned above, the water droplet generation system 20 also comprises a water temperature and pressure controller 22. The water temperature and pressure controller 22 is arranged to control the tank heater 23, the trace heater 27, the pump 21 and the pressure-reducing valve 28 to control the temperature and pressure of water in the tank 24 and in the supply line 26.

With reference now to FIGS. 3a and 3b, the nozzle device 14 will now be described in more detail. FIG. 3a shows a perspective view of the nozzle device 14. The nozzle device 14 of this embodiment comprises a first nozzle 31a, a second nozzle 31b, and a third nozzle 31c. The nozzles 31a, 31b, 31c are connected to a nozzle device body 32.

As can be seen in FIG. 3b, which shows the nozzle device 14 in cross-section, the nozzle device body 32 defines a nozzle device reservoir 34 within it. The nozzle device reservoir 34 is a space within the nozzle device body 32 that can receive water from the water supply line 26. So that the nozzle device reservoir 34 can receive this water, it is fluidly connected to the water supply line 26 via a water supply line connector 33 of the nozzle device 14. Thus, water can enter the water supply line connector 33 from the water supply line 26, flow into the nozzle device reservoir 34 and be ejected from the nozzle device 14 via the nozzles 31a, 31b, 31c.

Each nozzle 31a, 31b, 31c is substantially the same as each other nozzle 31a, 31b, 31c, and so only the first nozzle 31a (hereinafter the "nozzle") will be described in detail here. The nozzle 31a is shaped as a hollow cone. As mentioned above, the nozzle 31a is fluidly connected at one end to the nozzle device reservoir 34. At its other end, the nozzle 31a defines a nozzle outlet 35a. Thus, water can escape from the nozzle device reservoir 34, through the nozzle 31a and out of the nozzle outlet 35a.

Segments

Figure 4A:
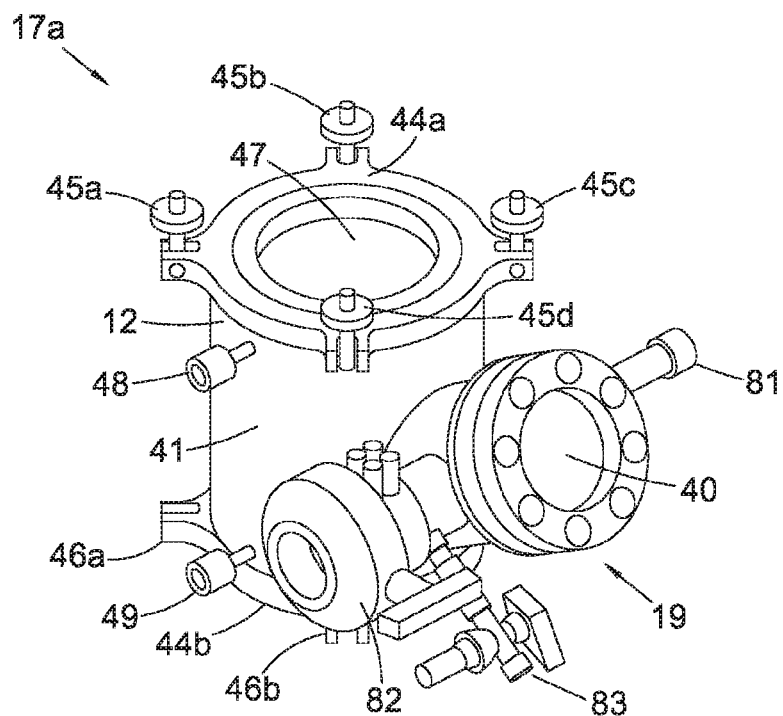
FIG. 4a shows a perspective view of a tubular segment of the ice accretion apparatus, the tubular segment in the form of a first wall section with a viewing port.
Figure 4B:
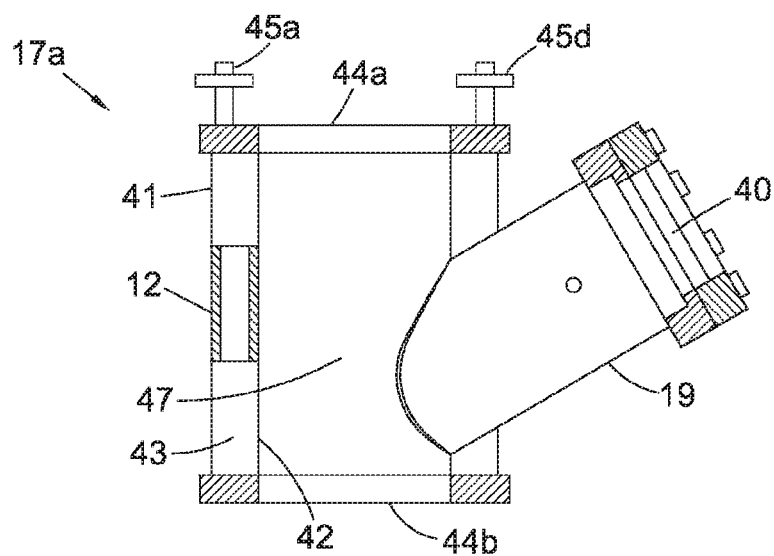
FIG. 4b shows a cross-sectional view of the first wall section with the viewing port.

With reference now to FIGS. 4a and 4b, the first wall section 17a will now be described in more detail. As can be seen in FIG. 4a, which is a perspective view of the first wall section 17a, the first wall section 17a has a body 41 that is substantially circular-cylindrical and defines a first wall section chamber portion 47 within it. This body 41 is made up of a wall 12, an inner wall 42, and first and second flanges 44a, 44b. This can be more easily seen in FIG. 4b, which shows the first wall section in cross-section. The wall 12 is circular-cylindrical in shape. That is, the wall 12 is a circular annulus in cross-section. The inner wall 42 is also circular-cylindrical in shape. The inner wall 42 has a smaller diameter than the wall 12. The inner wall 42 sits within the wall 12. The inner wall 42 and the wall 12 are spaced so as to define a cavity 43 between them. The inner wall 42 and the outer wall 12 are joined at their ends by first and second flanges 44a, 44b. The first and second flanges 44a, 44b can best be seen in FIG. 4a, although only part of the second flange 44b can be seen in this figure. The first and second flanges 44a, 44b are each annular in shape. They are each wide enough to span the gap between the wall 12 and the inner wall 42. The first and second flanges 44a, 44b are arranged to seal this gap. In this way, as just mentioned, the inner wall 42 and outer wall 12 define a cavity between them, which is sealed by the first and second flanges 44a, 44b. The first flange 44a is at one end of the wall 12 and inner wall 42, and the second flange 44b is at the end of the wall 12 and inner wall 42 that is distal the end to which the first flange 44a is fixed.

The wall 12 has an inlet in the form of a first valve 49 and an outlet in the form of a second valve 48. The first valve 49 is arranged to be connected to a supply of cooling fluid (not shown). In this embodiment, the cooling fluid is liquid nitrogen and the liquid nitrogen is supplied by a first liquid nitrogen transfer line that can be connected to the first valve 49 via a first transfer tube. The second valve 48 is arranged to be connected to a second liquid nitrogen transfer line via a second transfer tube. In other embodiments, it is envisaged that the inlet and the outlet may be located in other positions than those shown in the Figures. In one such other embodiment, the inlet is located at the position of the first valve 49 of this embodiment, and the outlet is located at the position of the second valve 48.

The first and second flanges 44a, 44b comprise connectors by which they can be connected to corresponding flanges on other parts of the icing device 10. The first flange 44a comprises four male fixings 45a, 45b, 45c, 45d. These can be most easily seen in FIG. 4a. They are equally spaced from one another around the exterior of the first flange 44a. The four male fixings 45a, 45b, 45c, 45d are substantially the same as one another, and so only one 45a of the male fixings 45a, 45b, 45c, 45d will be described in detail here. The male fixing 45a is made up of a nut and bolt. The bolt is pivotally attached to the first flange 44a. The nut is positioned on the bolt. The bolt is threaded so that the nut can be tightened on the bolt.

The second flange 44b comprises four female fixings 46a, 46b (of which only two can be seen in the figures). The four female fixings 46a, 46b are equally spaced from one another around the exterior of the second flange 44b. The four female fixings 46a, 46b are substantially the same as one another and so only one 46a of the female fixings 46a, 46b will be described in detail here. The female fixing 46a is arranged to receive the bolt of a male fixing such as the male 45 fixing described above. The female fixing 46a is shaped as two prongs between which the bolt of the male fixing 45a can be pivoted.

The second 17b and third 17c wall sections are substantially the same as the first wall section 17a except that they do not comprise a viewing port 19. The female fixings of the second wall section 17b are arranged to be connected to the male fixings 45a, 45b, 45c, 45d of the first wall section 17a. The female fixings of the third wall section 17c are arranged to be connected to the male fixings of the second wall section 17b.

In other embodiments, a tubular segment (wall section 17) may be releasably connected to an adjacent component using a connection system which is different to the system of male fixings and female fixings described above. For example, the connection system may comprise: removable clamps for clamping together adjacent flanges of adjacent components; a removable circumferential band for clipping together the adjacent flanges of adjacent components; or one component may be screwed directly to an adjacent component, e.g. the bottom end of one tubular segment may screw directly into the top end of another tubular component.

As mentioned above, the first wall section 17a comprises a viewing port 19 connected to the body 41. In this embodiment, the viewing port 19 takes the form of a single-walled tube. One end of the tube of the viewing port 19 is connected to the inner wall 42 and wall 12 of the first wall section 17a. The other end of the tube of the viewing port 19 is closed by a viewing window 40 which is, in this embodiment, made of a transparent glass that is resistant to low temperatures, such as borosilicate glass. The inner wall 42 and wall 12 of the first wall section 17a define a hole where the viewing port 19 is connected to them so that the first wall section chamber portion 47 can be viewed through the viewing window 40.

The viewing port 19 also comprises an overpressure protector 81 to which a pressure gauge (not shown) can be connected to gauge pressure within the chamber 18, a butterfly valve 82 to which a vacuum pump (not shown) can be connected to reduce pressure within the chamber 18, and a dry nitrogen connection valve 83 to which a dry nitrogen supply (not shown) can be connected to purge the chamber 18 and thereby reduce moisture within the chamber.

Each of the first 17a, second 17b and third 17c wall sections has chamber heating means in the form of an electric heater jacket arranged circumferentially around the wall section 17a, 17b, 17c. The electric heater jackets are not shown in the figures. In another embodiment, in addition to the electric heater jackets, the icing device also has an insulated jacket around each of the wall sections. This helps to reduce heat transfer between the chamber and the environment, and therefore provides for more energy-efficient and faster heating and cooling than in embodiments in which the insulated jackets are not present.

Top Unit

With reference once more to FIG. 1, the configuration of the top unit—the droplet discharge device holder 13—of the icing device 10 will now be described in more detail. The droplet discharge device holder 13 is shaped as a circular plate. Its outer diameter is the same as the outer diameter of the top flange of the third wall section 17c. The droplet discharge device holder 13 sits on top of the third wall section 17c to act as a lid to the chamber 18 defined by the first, second and third wall sections 17a, 17b, 17c. The droplet discharge device holder has four, evenly-spaced, female fixings around its circumference. These female fixings are substantially the same as the four female fixings 46a, 46b that form a part of the first wall section. They are arranged to mate with corresponding male fixings on the third wall section 17c.

In this embodiment, the droplet discharge device holder 13 also includes the nozzle device 14. The nozzle device 14 is arranged so that its nozzles 31a, 31b, 31c are inside the chamber 18 when the droplet discharge device holder 13 is in place on the third wall section 17c. The water supply line connector 33 of the nozzle device 14 extends through the droplet discharge device holder 13 so that it can be connected to the water supply line 26 outside the chamber 18.

Finally, the droplet discharge device holder 13 also comprises a pressure sensor and a temperature sensor, which in this embodiment are combined in a single sensor device 101. The sensor device 101 extends through the droplet discharge device holder 13 such that it can sense the pressure and temperature within the chamber 18.

Ice Adhesion Test Device

Figure 5A:
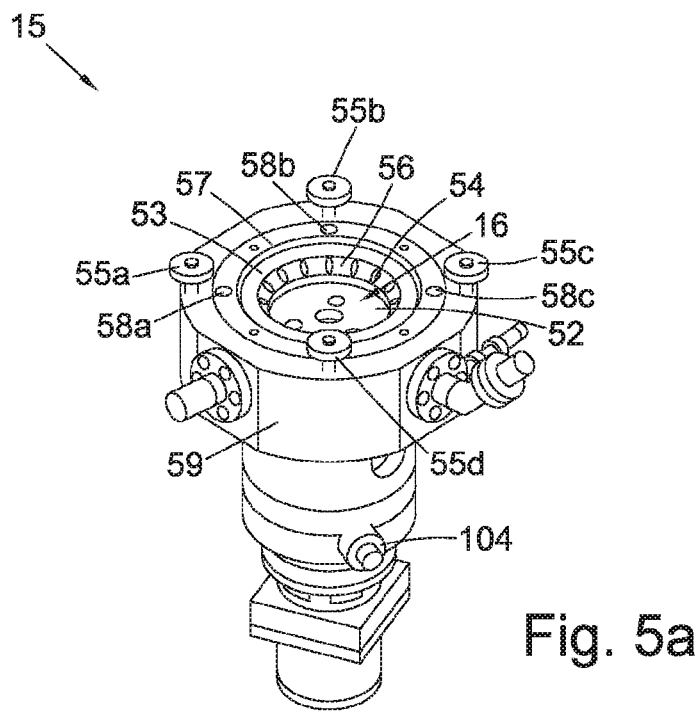
FIG. 5a shows a perspective view of a bottom unit of the ice accretion apparatus, the bottom unit in the form of an ice adhesion test device.
Figure 5B:
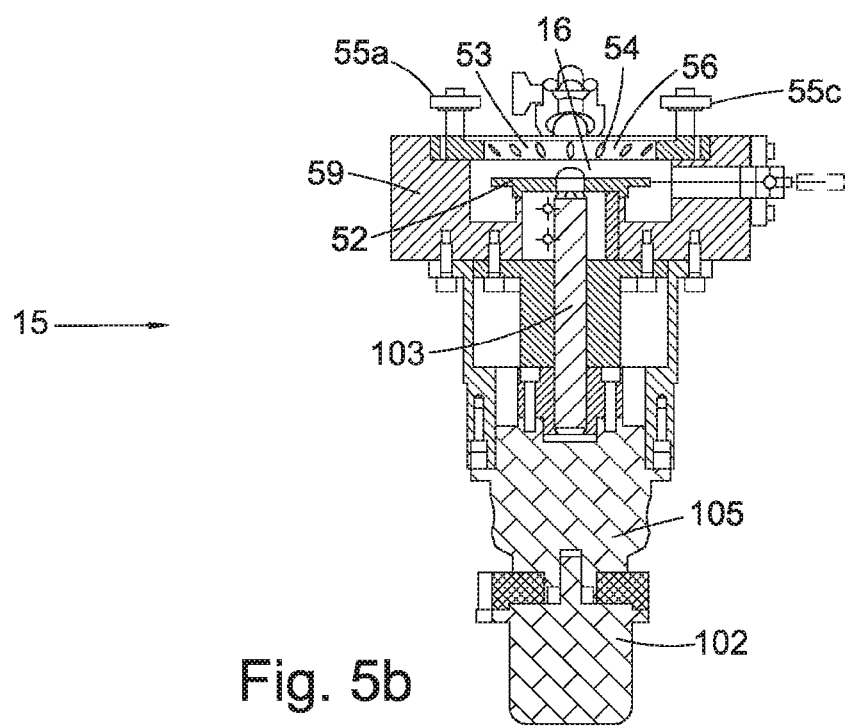
FIG. 5b shows a cross-sectional view of the ice adhesion test device.
Figure 6A:
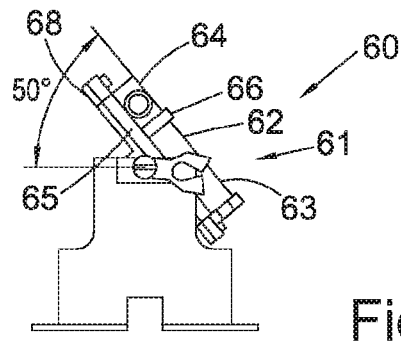
FIGS. 6a to 6d show different perspective views of an alternative bottom unit of the ice accretion apparatus, the alternative bottom unit in the form of an ice runback test device.
Figure 6B:
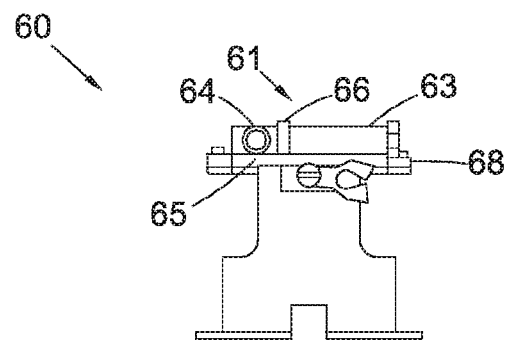
Figure 6C:
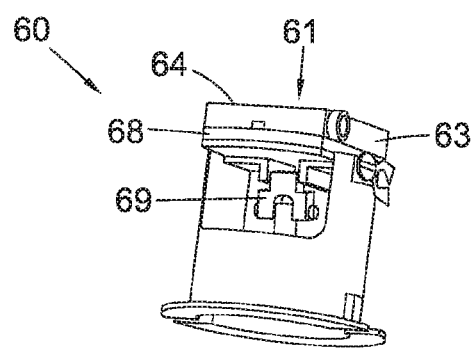
Figure 6D:
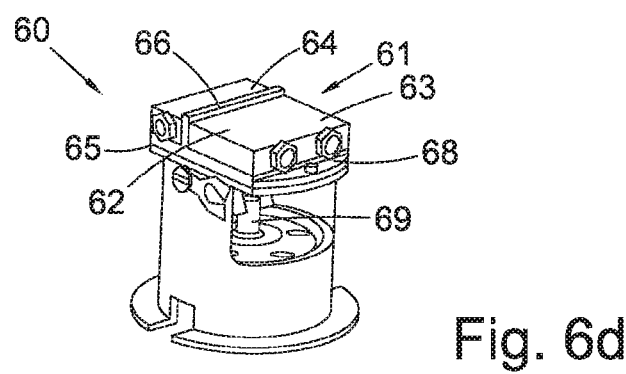

FIGS. 5a and 5b show, respectively, a perspective and a cross-sectional view of the ice adhesion test device 15. The ice adhesion test device 15 will now be described with reference to these figures. As mentioned above, the ice adhesion test device 15 forms the bottom unit of the icing device 10. It is arranged to be releasably fastened to the first wall section 17a by male fixings 55a, 55b, 55c, 55d evenly spaced around the top of the body 59 of the ice adhesion test device 15 in positions corresponding to the female fixings 46a, 46b on the second flange 44b of the first wall segment 17a. The male fixings 55a, 55b, 55c, 55d of the ice adhesion test device 15 are substantially the same as the male fixings 45a, 45b, 45c, 45d of the first flange 44b of the first wall segment 17a and so will not be described in further detail here.

As mentioned above in relation to FIG. 1, the ice adhesion test device 15 comprises a target in the form of a well 16. The well 16 is made up of a sample plate 52 and an ice-engagement element in the form of a well side wall 53. The sample plate 52 is substantially circular. It comprises screw-holes to receive screws to enable a sample (not shown) to be fixed to it. The well side wall 53 is defined by an annulus positioned circumferentially around the sample plate 52. The well side wall 53 is also substantially circular. It surrounds the sample plate 52 around the circumference of the sample plate 52. The well side wall 53 has two portions: an inner portion 56, and an outer portion 57. The inner portion 56 is located radially inwardly of the outer portion 57. The inner portion 56 is also axially offset from the outer portion 57, so that the when the ice adhesion test device 15 is assembled, the inner portion 56 is axially (as well as radially) closer than the outer portion 57 to the sample plate 52. The inner portion 56 of the well side wall 53 slopes radially outward away from the sample plate 52.

The inner portion 56 of the well side wall 53 has several recesses 54 on the side of the well side wall 53 closest to the sample plate 52. The recesses 54 are provided to key with ice formed in the well 16 so as to hold the ice substantially stationary with respect to the well side wall 53. In this embodiment, it has sixteen recesses 54. In other embodiments, there may be other numbers of recesses. There may be conceivably any number of recesses provided that the number of recesses is sufficient to key with ice formed in the well 16 and thus to hold it stationary with respect to the well side wall 53. In this embodiment, each recess 54 is substantially the same as each other recess. In this embodiment, the recesses 54 are equally spaced from one another around the inner portion 56 of the well side wall 53.

The outer portion 57 of the well side wall 53 is stepped. The radially-innermost part of the outer portion 57 meets the inner portion 56 at an angle of more than 90° to the inner portion 56. It lies in a plane parallel to the sample plate 52. The radially-outermost part of the outer portion 57 is stepped relative to the radially innermost part so that it is axially above the radially-innermost part. This enables the radially-outermost part of the outer portion 57 to sit flush with the top of the body 19 of the ice adhesion test device 15. The radially-outermost part of the outer portion 57 comprises holes 58a, 58b, 58c, 58d for receiving screws to connect the well side wall 53 to the body 59 of the ice adhesion test device 15.

In the present embodiment, the inner diameter of the inner portion 56 of the well side wall 53 is fixed. The inner diameter is, in the present embodiment, about 40 mm (millimeters). In an alternative embodiment, the inner diameter of the inner portion 56 of the well side wall 53 can be varied to adjust for different sample sizes or to expose different surface areas of a sample fixed to the sample plate 52. In one such alternative embodiment, the inner diameter of the inner portion 56 of the well side wall 53 is adjustable between about 40 mm and about 100 mm.

The side wall 53 is connected to the top of the body 59 of the ice adhesion test device 15 such that when the ice adhesion test device 15 is connected to the first wall section 17a of the icing device 10, the well 16 formed by the sample plate 52 and side wall 53 is at the bottom of the chamber 18 of the icing device 10. Axially below the sample plate 52, and within the body 59 of the ice adhesion test device 15, is torque means in the form of a motor 102. The motor 102 is of a sort that could readily be implemented by the person skilled in the art without further explanation, and which is thus indicated by cross-hatching in FIG. 5b. The sample plate 52 is connected to the motor 102 via gearing 105 (again of a sort which could readily be implemented by the person skilled in the art and therefore indicated only by cross-hatching) by a shaft 103. The motor 102 is arranged so that it can rotate the sample plate 52 relative to the side wall 53.

The ice adhesion test device 15 also comprises transducer means in the form of a torque ring 104, partially visible in FIG. 5a. The torque ring 104 is arranged to measure the torque on the shaft 103, and to measure both lateral and axial stresses on the shaft.

Assembly

With reference once more to FIG. 1, the assembly of the icing device 10 will now be described.

First, a sample to be tested—in this embodiment, a disc of aluminium NS4 coated with a potentially ice-phobic material—is secured to the sample plate 52. In other embodiments, the sample can be made up of a substrate other than aluminium NS4, and/or a different potentially ice-phobic material. For example, substrate may be a composite material, glass, steel or plastic such as polycarbonate, polyether ether ketone (PEEK) or acrylic.

To assemble the remainder of the icing device 10, the ice adhesion test device 15 is secured to a lab bench (not shown), for example by fitting the body 59 of the ice adhesion test device 15 into a hole in the lab bench. The first wall section 17a is then fitted on top of the ice adhesion test device 15 by attaching the male fixings 55a, 55b, 55c, 55d of the ice adhesion test device 15 to the female fixings 46a, 46b on the second flange 44b of the first wall segment 17a. Next, the second wall section 17b is fitted on top of the first wall section 17a, and the male fixings 45a, 45b, 45c, 45d of the first wall section 17a are secured to the female fixings of the second wall section 17b. Then, the third wall section 17c is fitted on top of the second wall section 17b, and the male fixings of the second wall section are secured to the female fixings of the third wall section 17c. After this, the nozzle device holder 13 is fitted on top of the third wall section 17c and secured in a similar manner. This provides a sealed chamber 18 within the column.

The first (inlet) valves (not shown in FIG. 1) of each of the wall sections are each connected to a transfer tube (not shown) and, via this, to a liquid nitrogen transfer line (not shown). The second (outlet) valves (also not shown) are also each connected to a liquid nitrogen transfer line (again, not shown). The tank 24 (shown in FIG. 2) is filled with distilled water. The water supply line connector 33 of the nozzle device 14 (shown in FIGS. 3a and 3b) is connected to the water supply line 26 (shown in FIG. 2).

Operation

With continued reference to FIG. 1, and with reference, too, to FIG. 4a, the operation of the bench-top ice testing device 10 will now be described.

The chamber 18 is purged of moisture by supplying dry nitrogen through the dry nitrogen connection valve 83. Pressure inside the chamber is reduced by a vacuum pump connected to the butterfly valve 82. The pressure within the chamber can be read from a pressure gauge connected to the overpressure protector 81.

Liquid nitrogen enters the cavity 43 of the first wall section 17a via the first valve 49, cools the first wall section chamber portion 47 and exits the cavity 43 via the second valve 48. The chamber portions defined by the second 17b and third 17c wall sections are cooled by a corresponding operation involving the corresponding valves and cavities of these wall sections 17b, 17c. In this way, the whole of the chamber 18 within the column 11 is cooled. In this embodiment, the flow rate of the liquid nitrogen to the cavity of the first wall section 17a is selected such that the part of the chamber 18 defined by the first wall section 17a is cooled to about −17.5° C. In this way, the part of the chamber 18 defined by the first wall section 17a, which is closest to the sample plate 52, is cold enough that water droplets will freeze on the surface of the sample plate 52. The flow rate of the liquid nitrogen to the cavity of the second wall section 17b is selected such that the part of the chamber 18 defined by the second wall section 17b is cooled to about 0° C. The flow rate of the liquid nitrogen to the cavity of the third wall section 17c is selected such that the part of the chamber 18 defined by the third wall section 17c is cooled to about 10° C. so that water in the nozzle device reservoir 34 and the nozzles 31a, 31b, 31c will not freeze.

In other embodiments, the flow rate of the liquid nitrogen to the cavity of the first wall section 17a is selected such that the part of the chamber 18 defined by the first wall section 17a is cooled down to −40° C., which is accepted as the lowest temperature at which supercooled liquid water droplets are likely to occur in the atmosphere. This ensures that the water droplets formed by the nozzle device 14 freeze on contact with the sample plate 52. For example, in embodiments in which it is desired to produce clear ice on the sample plate 52, the part of the chamber 18 defined by the first wall section 17a is cooled to between 0° C. and −5° C. In embodiments in which it is desired to produce clear or mixed ice on the sample plate 52, the part of the chamber 18 defined by the first wall section 17a is cooled to between −5° C. and −10° C. In embodiments in which it is desired to produce mixed or rime ice on the sample plate 52, the part of the chamber 18 defined by the first wall section 17a is cooled to between −10° C. and −15° C. In embodiments in which it is desired to produce rime ice on the sample plate 52, the part of the chamber 18 defined by the first wall section 17a is cooled to between −15° C. and −40° C. In these other embodiments, the flow rate of the liquid nitrogen to the cavity of the third wall section 17c is selected such that the part of the chamber 18 defined by the third wall section 17c is cooled to conceivably any temperature at which the water in the nozzle device reservoir 34 and the nozzles 31a, 31b, 31c will not freeze, provided that the temperature is not so high that droplets formed by the nozzle device 14 do not freeze on contact with the sample plate 52. For example, in one such other embodiment, the flow rate of the liquid nitrogen to the cavity of the third wall section 17c is selected such that the part of the chamber 18 defined by the third wall section 17c is cooled to 15° C.

In still further embodiments, other techniques are employed to create a temperature gradient (for example one of the above temperature gradients) within the chamber 18.

In one such further embodiment, two or more different cooling fluids are used. In particular, a cooling fluid having one boiling point is passed through the cavity 43 of the first wall section 17a (entering via the first valve 49 and exiting via the second valve 48), and a different cooling fluid with a higher boiling point is passed through the cavities of the second 17b and third 17c wall sections. Alternatively, a cooling fluid having one boiling point is passed through the cavity 43 of the first wall section 17a and through the cavity of the second wall section 17b, and a different cooling fluid with a higher boiling point is passed through the cavity of the third 17c wall section.

The fluid passed through the cavity 43 of the first wall section 17a could be, for example, liquid nitrogen, with the fluid passed through the cavity of the third wall section 17c being, for example, liquid argon (and either fluid being used for the second wall section 17b). In another example, the fluid passed through the cavity 43 of the first wall section 17a could be, for example, helium-4, with the fluid passed through the cavity of the third wall section 17c being, for example, liquid nitrogen (and either fluid being used for the second wall section).

In another such further embodiment, a cooling fluid (such as liquid nitrogen) is first passed through the cavity 43 of the first wall section 17a to cool the part of the chamber 18, and is then recirculated through the cavity of the second wall section 17b and then the third wall section 17c. In this way, the cooling fluid is heated as it passes through each cavity. Thus, it provides reduced cooling to each part of the chamber 18 defined by the successive wall sections through the cavity of which the cooling fluid passes.

In yet another such further embodiment, one or more of the heater jackets is operated to heat a portion of the chamber. For example, the heater jacket around the third wall section 17c can be operated to increase the temperature of the portion of the chamber 18 defined by this wall section 17c with respect to temperatures of the portions of the chamber 18 defined by the first 17a and second 17b wall sections. In another example, the heater jackets around the third wall section 17c and the second wall section 17b are both operated, but at different temperatures. Specifically, the heater jacket around the third wall section 17c is operated at a higher temperature than the heater jacket around the second wall section 17b, so as to increase the temperature of the portion of the chamber 18 defined by the third wall section 17c with respect to the temperature of the portion of the chamber 18 defined by the second wall sections 17b, which is in turn increased with respect to the temperature of the portion of the chamber 18 defined by the first wall section 17a.

Returning now to the description of the operation of the first-described embodiment of the bench-top ice testing device 10, water in the tank 24 is heated by the tank heater 23. Water is pumped by the pump 21 from the tank 24 into the water supply line 26. The water is further heated in the water supply line 26 by the trace heater 27. In this embodiment, the water is heated to a temperature of about 40° C. In other embodiments, the water can be heated to other temperatures. It is envisaged that the water be heated to a temperature which is high enough that the water does not freeze on contact with the nozzles 31a, 31b, 31c. The nozzles 31a, 31b, 31c would otherwise be cold enough to freeze at least some of the water since they are within the cooled chamber 18. In particular, it is envisaged that the water be heated to a temperature between about 20° C. and 95° C.

The water enters the nozzle device reservoir 34 and each of the nozzles 31a, 31b, 31c. The pressure applied to the water by the pump 21 causes it to exit the nozzle outlets 35a, 35b, 35c, producing water droplets in a spray.

In this way, water droplets of a specified size—in this embodiment, the droplets have a diameter of about 10 to 50 microns ($10 \times 10^{-6}$ m to $50 \times 10^{-6}$ m), with an average diameter of around 35 microns ($35 \times 10^{-6}$ m)—are ejected from the nozzle device 14. The speed of the droplets is increased by the increased pressure in the nozzle device reservoir 34 created by the pump 21. The increased pressure in the nozzle device reservoir 34 also affects the size of the water droplets generated. In particular, by increasing the pressure in the nozzle device reservoir 34, the droplet size is decreased. In other embodiments, other droplet diameters may be desired. These can be achieved by increasing or decreasing the pressure in the nozzle device reservoir using the pump 21. Alternatively, or in addition, an alternative nozzle device can be used, with nozzle outlets of a different diameter to those of the present embodiment.

The droplets travel vertically downwards through the chamber 18 towards the well 16 of the ice adhesion test device 15, and the sample within this well 16. As the water droplets travel through the chamber 18, they are supercooled. When they impact the sample plate 52, they freeze. In this embodiment, due to the particular selection of water droplet size and chamber 18 temperature, rime ice is formed on the sample. The ice formed on the sample plate 52 can be viewed through the viewing port 19 to determine when sufficient ice has accreted to stop operation of the nozzle device 14. The nozzle device 14 continues to be operated as described above until a layer of rime ice is formed on the sample and on the side wall 53 of the well 16. The rime ice also enters the recesses 54 in the side wall 53 of the well 16. The gate valve 25 in the supply line 26 (shown in FIG. 2) is then closed, and the pump 21 switched off. Thus, the formation of droplets is stopped.

In other embodiments, the droplet diameter and temperature gradient within the chamber 18 are different, such that other types of ice are formed in the well 16. For example, when cooled water droplets impact the surface of the sample plate 52 and side wall 53 and wet the surface before freezing, glaze ice is formed.

In yet other embodiments, in order to simulate icing conditions in which rain falls and is subsequently frozen, water droplets are formed (substantially in the manner described above) before the chamber is cooled. Thus, the water droplets impact the sample plate 52 without freezing, and are only subsequently frozen by cooling the chamber 18 in the manner described above.

In still other embodiments, rather than generating a substantially continuous spray of water droplets (as described above), the flow of water to the nozzle device reservoir 34 and each of the nozzles 31a, 31b, 31c is periodically interrupted by closing the gate valve 25. For example, in one of these embodiments, water is pumped by the pump 21 to the nozzles 31a, 31b, 31c (and heated) as described above. The gate valve 25 is opened for 5 seconds, and then closed for 10 seconds. This opening and closing of the gate valve 25 is repeated. Thus, a spray of water droplets falls on the sample plate 52 for 5 seconds, at 10-second intervals. This method can be used to create layers of ice on the sample plate 52, since the water droplets that have fallen on the sample plate 52 have time to freeze (while the gate valve 25 is closed) before the spray of water droplets is resumed.

Returning to the description of the first-described embodiment, next, the shear strength with which the ice is adhered to the sample is measured using the ice adhesion test device 15. With reference now to FIGS. 5a and 5b, the operation of the ice adhesion test device 15 will now be explained. Power is supplied to the motor 102 so that it applies torque to try to turn the shaft 103, and thus the sample plate 52. The recesses 54 in the side wall 53 of the well 16 prevent rotation of the layer of rime ice relative to side wall 53. The motor 102 thus acts against the ice adhered to the sample. The torque at which the ice separates from the sample plate 52 is measured by the torque ring 104. From the measured torque at which the ice separates from the sample plate 52, the shear strength of adhesion of ice to the sample plate 52, and the stress on the ice when it separates from the sample plate 52 can be calculated.

Thus, the above-described embodiment provides a bench top icing device 10 that produces water droplets of a specified size at a specified temperature. The ice adhesion test device 15 can be used in conjunction with the bench top icing device 10 to determine the shear strength with which ice adheres to a sample.

In this embodiment, once the test has been run, the flow of liquid nitrogen into the transfer lines is turned off. Thus, the supply of liquid nitrogen to the cavity within each wall section is stopped and the chamber 18 is no longer cooled. Next, the ice adhesion test device 15 is removed from the first wall section 17a. The electric heater jackets around each of the wall sections are then switched on. In this way, the cavity 18 is heated. This enables the cavity 18 to be dried out before the next test is run. In other embodiments, depending on the desired temperature within the cavity 18 during a test, the flow of liquid nitrogen into the transfer lines can be turned off before a test or during a test.

Runback Ice Test Device

It is envisaged that other bottom units can be used with the icing device 10 as described above. In a second embodiment, the bottom unit of the ice accretion apparatus is in the form of a runback ice test device. The ice accretion apparatus of this embodiment is in the form of an icing device 10 as described above, but a runback ice test device is connected to the body 59 of the ice adhesion test device.

The runback ice test device in this embodiment is made up of a runback ice test fitting 60, and the same motor 102 and gearing 105 as used in the ice adhesion test device 15. In other embodiments, a dedicated motor and gearing can be used for the runback ice test device. The runback ice test fitting 60 is connected to the motor 102 (this is not shown in the figures) as will be described in more detail below.

FIGS. 6a to 6d show different perspective views of the runback ice test fitting 60. The runback ice test fitting 60 will now be described with reference to these figures. The runback ice test fitting 60 comprises a target in the form of a platform 61. The platform 61 can be most clearly seen in FIG. 6d. In this embodiment, the platform 61 is rectangular. The platform 61 has an upper face 62. The platform 61 is divided into two sections: a first section 63 and a second section 64. The first 63 and second 64 sections are both rectangular. The first 63 and second 64 sections are of the same width and depth. In this embodiment, the first section 63 is longer than the second section 64. The first section 63 therefore has a greater surface area than the second section 63.

In this embodiment, the platform 61 has a thickness of about 2 mm, a width of about 58 mm, and a length of about 45 mm. In other embodiments, the platform 61 may have different dimensions, provided that these are not so great that the platform 61 does not fit within the chamber 18.

The first 63 and second 64 sections of the platform 61 are arranged on a thermally insulating component 65. The thermally insulating component 65 is, in this embodiment, made from polytetrafluoroethylene (PTFE), although other materials with good thermal insulation properties can be used in other embodiments. The thermally insulating component 65 has a base 66 shaped as a rectangle with an area sufficient to accommodate the first 63 and second 64 sections of the platform 61. The thermally insulating component 65 also has a protrusion 66. The protrusion 66 provides a protruding thermal barrier between the first section 63 and the second section 64 of the platform 61. The protrusion 66 runs from one of the longer sides of the base 66 to the opposite side. In other words, the protrusion 66 runs across the width of the platform 61. It has substantially flat sides against which the first section 63 and second section 64 of the platform 61 abut. The protrusion 66 has a height which is slightly greater than the height of the first 63 and second 64 sections of the platform 61 so that it protrudes above the upper face 62 of the platform.

The first 63 and second 64 sections of the platform 61 have heater elements within them (not shown). The heater elements are independently-controllable electric heaters. They are arranged to heat the upper face of the platform 61. The heater elements are each connected to a heater means controller in the form of a heater elements controller (also not shown). The heater elements controller is arranged to switch the heater elements on and off independently of each other. In this embodiment, the heater elements controller is additionally arranged to control the temperature to which each of the heater elements is heated.

The thermally insulating component 65 with the platform 61 mounted on top of it is in turn mounted to a pivoting plate 68. The pivoting plate 68 is pivotally mounted to platform inclination means made up of, in this embodiment, the motor 102, gearing 105 and a coupling 69 (the motor 102 and gearing 105 are not shown in FIGS. 6a to 6d). The coupling 69 connects the pivoting plate 68 via the gearing 105 to the motor 102. The coupling 69 and gearing 105 are arranged such that the turning of the motor 102 inclines the pivoting plate 68 so that the second section 64 of the platform is above the first section 63 of the platform. The coupling 69 is arranged to hold the pivoting plate 68 in the inclined position when the motor 102 stops turning.

Assembly

The bench-top icing device to be used with the ice runback test device is assembled substantially as described above in relation to the icing device 10 to be used with the ice adhesion test device 15, except that the ice runback test device is substituted for the ice adhesion test device 15 during assembly.

Operation

With reference to FIGS. 1 and 6, the operation of the bench-top ice testing device of this second embodiment will now be described. First, the platform 61 is positioned. The motor 102 is made to turn. This turning of the motor 102 causes the coupling 69 to pivot the pivoting plate 68 such that the second section 64 of the platform 61 is above the first section 63 of the platform 61. In this embodiment, the pivoting plate 68 is pivoted to an angle of 50°, although in other embodiments the pivoting plate 68 can be pivoted to other angles to test runback ice at these other angles. When the pivoting plate 68 has been pivoted to the desired angle, the motor 102 is stopped.

Next, the chamber 18 is cooled substantially as described above, using liquid nitrogen. The heater element of the first section 63 of the platform 61 is switched on. In this particular embodiment, the first section 63 is heated to a temperature of about 30° C. In other embodiments, the first section 63 can be heated to other temperatures. It is envisaged that the first section 63 be heated to a temperature that is representative of an electro-thermal ice protection system that would be used with the potentially ice-phobic coating.

Super-cooled or cooled droplets are then created substantially as described above in relation to the first embodiment; that is by ejecting droplets of water from the nozzle device 14.

The droplets are deposited on the platform 61. Since the second section 64 of the platform 61 is unheated, the droplets form rime ice on the second section 64. In other embodiments, as discussed above, glaze ice or a mixture of glaze ice and rime ice is formed on the second section 64. Since the first section 63 of the platform 61 is heated, no ice is formed on the first section 63. The protrusion 66 prevents ice formed on the second section 64 from extending onto the first section 63 of the platform 61. The protrusion 66 acts as a thermal barrier between the first section 63 and the second section 64.

As in the first embodiment, the accretion of ice can be viewed through the viewing port 19. When sufficient ice is determined to have been deposited on the second section 64 of the platform 61, operation of the nozzle device 14 is stopped (as described above in relation to the first embodiment). Thus, no more droplets land on the platform 61.

The heater element of the first section 63 of the platform 61 is switched off. The first section 63 is allowed to cool to, in this embodiment, a temperature of about −15° C. In other embodiments, other temperatures can be selected, depending on the atmospheric conditions that an operator wishes the test to approximate. For example, in other embodiments, the first section 63 can be allowed to cool to a higher temperature than in this embodiment: between 0° C. and −15° C. The heater element of the second section 64 of the platform 61 is switched on. The ice that was formed on the second section 64 begins to melt. Water from the melting ice runs downwards, over the protrusion 66 and on to the first section 63 of the platform 61. The water freezes on the first section 63 of the platform 61, forming runback ice.

In other embodiments, other angles of the pivoting plate 68 and other temperatures to which the first 63 and second 64 sections are heated and cooled can be selected, and different thicknesses of ice can be allowed to build up on the second section 64. In this way, the formation and behaviour of runback ice can be studied under many different conditions.

Once the test has been run, the flow of liquid nitrogen into the transfer lines is turned off. Thus, the supply of liquid nitrogen to the cavity within each wall section is stopped and the chamber 18 is no longer cooled. As in the first embodiment, the electric heater jackets around each of the wall sections are switched on such that the cavity 18 is heated and dried out before the next test is run. The ice runback test device is then removed from the body 59. In other embodiments, depending on the desired temperature within the cavity 18 during a test, the flow of liquid nitrogen into the transfer lines can be turned off before a test or during a test.

Other Embodiments

It is envisaged that the ice accretion apparatus may include, in other embodiments, additional components, or that some of its components may be replaced with alternative components.

For example, in one such alternative embodiment, the ice accretion test device, still in the form of a bench-top icing apparatus, additionally has an insulated jacket around each section of the column.

In another alternative embodiment, the apparatus comprises valve means for introducing a volume of gas into the chamber and for sealing the volume of gas in the chamber. The valve means is in the form of a two-way valve that extends through a wall of the chamber, for example through the viewing port of the apparatus, such that when open, it can connect the chamber within the bench-top icing device with an external gas supply and allow gas into the chamber. When closed, the two-way valve seals the chamber.

In yet another alternative embodiment, the apparatus comprises pumping means for producing a reduced pressure in the chamber. In this embodiment, the apparatus has a two-way valve extending through the wall of the chamber, for example through the viewing port of the apparatus. The pumping means is in the form of a vacuum pump. The vacuum pump is connected via a tube to the two-way valve. When open, and when the pump is switched on, the valve allows through gas from within the chamber. The pump sucks the gas through the valve and discharges it. In this way, the pressure within the chamber can be reduced. In this embodiment, the column is constructed to withstand pressures down to at least 14.1 kPa.

In a further alternative embodiment, the apparatus comprises a controller. In this embodiment, the controller is in the form of a microcontroller. The microcontroller is connected to a sensor device of the type described in relation to the first embodiment, so that it can receive pressure and temperature signals from the sensor device. The microcontroller is also connected to valve means and pumping means as described in relation to the two alternative embodiments just described so that it can control these and thereby control pressure within the chamber. Finally, the microcontroller is connected to chamber heating means as described above in relation to the first embodiment so that it can control this and thereby control the temperature within the chamber. The microcontroller is programmed to control the pressure and temperature based on signals from the sensor device.

In yet further alternative embodiments, the apparatus comprises more or fewer tubular segments.

For example, in one such alternative embodiment, the apparatus comprises only two tubular segments. One of these tubular segments is substantially the same as the first wall section described in relation to the first embodiment. The other tubular segment is substantially the same as the third wall section described in relation to the first embodiment. In this alternative embodiment, the height of the column is therefore smaller than the height of the column in embodiments in which there are three tubular segments (such as the first embodiment). This results in a more compact apparatus.

In a second such alternative embodiment, there are four tubular segments. The apparatus is substantially as described above in relation to the first embodiment, except that it has an additional wall section between the first and second wall sections. This additional wall section is substantially the same as the second and third wall sections of the first embodiment. The height of the column in this alternative embodiment is therefore greater than the height of the column in the first embodiment. This results in the droplets generated by the nozzle device having a higher velocity when they hit the target at the bottom of the column than they would in an icing device with fewer tubular segments.

Figure 7:
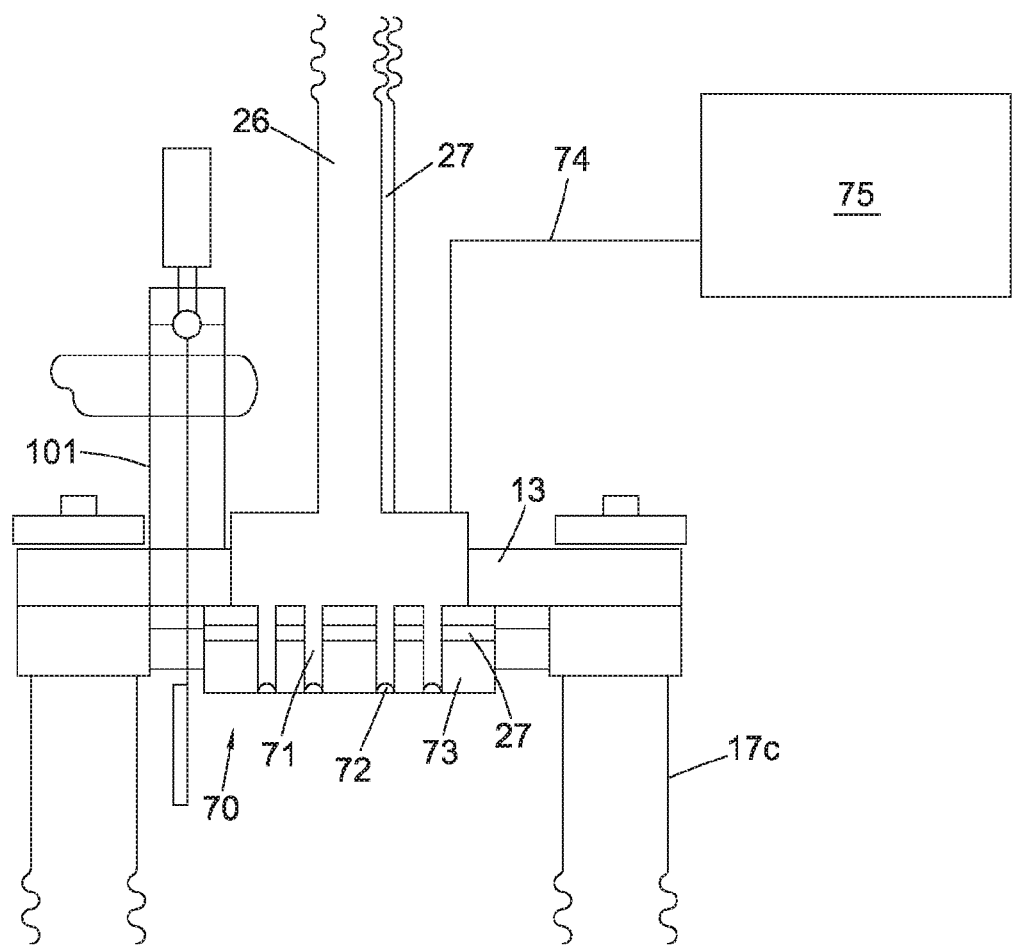
FIG. 7 shows a schematic cross-sectional view of an alternative droplet discharge device fitted to the top of the ice accretion apparatus.

In another alternative embodiment, the droplet discharge device is a piezoelectric device 70, instead of a nozzle device 14. The piezoelectric device 70 is shown schematically, in cross-section, in FIG. 7. With reference to this figure, the piezoelectric device 70 will now be described in more detail.

The piezoelectric device 70 is made up of a plate 73 with a number of through-holes in the form of water channels 71. The number of water channels 71 is selected to provide enough water droplets to provide the desired icing conditions, based on each water channel 71 producing one water droplet at a time (as will be explained further below).

In this embodiment, the diameter of the plate 73 is selected to be less than the diameter of the area to be sprayed with droplets, to account for the outward spread of water droplets. In another embodiment, however, the diameter of the plate 73 is selected to be substantially the same as the diameter of the area to be sprayed with droplets. The plate 73 has a trace heating element 27 around its circumference. This is in order to heat the plate 73.

Each water channel 71 contains a piezoelectric element in the form of a piezoelectric crystal 72. The piezoelectric crystals 72 are each arranged so that when a current flows through them, they bend so as to draw water from their respective water channel 71 into the space created by this deformation. When no current is supplied, the piezoelectric crystals 72 return to their original shape. The piezoelectric crystals 72 are each arranged so that when this occurs, they eject a droplet of water from their respective water channel 71. Each piezoelectric crystal 72 is connected via an electrical connection 74 to a combined power source and controller 75. This is in order to supply current from the power source and controller 75 to the piezoelectric crystals 72 and to control the magnitude of the current supplied.

The type of piezoelectric crystal 72 is selected according to the size of the droplet which it is desired to eject from a water channel 71. A piezoelectric crystal 72 which deforms relatively greatly under a given electric current will eject a relatively large volume of water when it relaxes after deformation. The type of piezoelectric crystal 72 is also selected according to the speed with which it is desired to eject a droplet from a water channel 71. In particular, a type of piezoelectric crystal 72 that relaxes relatively rapidly after deformation in response to a current being passed through it will eject a droplet through from a water channel 71 at a relatively great speed.

The piezoelectric device 70 is fitted into the droplet discharge device holder 13 in place of the nozzle device 14. The remainder of the water droplet generation system 20 to which the piezoelectric device is connected is substantially the same as that described above in relation to FIG. 2. In other words, the piezoelectric device 70 is connected to a water supply line 26 with a trace heater 27, and to a pump 21 and tank 24, and all the other components shown in FIG. 2.

In operation, water is supplied to the water channels 71 from the water supply line 26. The power source and controller 75 is operated to supply current, via the electrical connection 74, to the piezoelectric crystals 72. This bends the piezoelectric crystals 72 in a first direction so as to draw water from their respective water channel 71 into the space created by this deformation. The current through the piezoelectric elements 72 is then stopped so that they return to their original shapes and push the water out in the form of water droplets. The magnitude of the current supplied to the piezoelectric crystals 72 is selected using the controller 75 so as to determine the magnitude of deformation of the piezoelectric crystals 72. This, in turn, controls the size of the droplets produced by the piezoelectric device 70.

The invention claimed is:

1. Ice accretion apparatus comprising:
   a column having a longitudinal axis, a side wall, and a central chamber having top and bottom ends, wherein the side wall comprises a plurality of tubular segments and wherein the tubular segments are releasably stacked on top of one another;
   a top unit which closes the top end of the chamber and includes a droplet discharge device for producing water droplets;
   a bottom unit which closes the bottom end of the chamber and includes a target; and
   chamber cooling means configured to cool the chamber during a test and thereby to cool the water droplets, whereby, in use during the test, a layer of accreted ice is built up on the target.

2. Ice accretion apparatus of claim 1, wherein the chamber cooling means is one or more of (a) in being configured to cool the chamber during the test, configured to cool or super-cool the water droplets as they travel down the chamber from the droplet discharge device to the target; (b) configured to produce a temperature gradient between the top and bottom ends of the chamber; and (c) further comprising chamber heating means for heating the chamber between tests.

3. Ice accretion apparatus of claim 1, wherein the chamber cooling means comprises at least one wall cavity in the side wall and an inlet and an outlet for passing a cooling fluid through the at least one cavity.

4. Ice accretion apparatus of claim 1, further comprising temperature-control means for controlling the temperature of the water supplied to the droplet discharge device.

5. Ice accretion apparatus of claim 1, further comprising at least one of temperature sensor and a pressure sensor.

6. Ice accretion apparatus of claim 5, further comprising at least one controller arranged to receive signals output by one or both of the temperature sensor and the pressure sensor.

7. Ice accretion apparatus of claim 1, further comprising valve means for introducing a volume of fluid into the chamber and for sealing the volume of fluid in the chamber.

8. Ice accretion apparatus of claim 1, further comprising at least one of pumping means for producing a reduced pressure in the chamber, valve means for introducing a volume of gas into the chamber, pressurising means for controlling the pressure of water supplied to the droplet discharge device, and a viewing port arranged to allow observation from outside the apparatus of the target.

9. Ice accretion apparatus of claim 8, further comprising at least one controller arranged to at least one of (a) to control the chamber cooling means to control the temperature inside the chamber based on signals output to the at least one controller by at least one temperature sensor and (b) to control one or both of the valve means and the pumping means to control the pressure inside the chamber based on signals output to the at least one controller by the at least one pressure sensor.

10. Ice accretion apparatus of claim 1, wherein the column is releasably fitted to the bottom unit of the apparatus.

11. Ice accretion apparatus of claim 10, wherein the target is in the form of a well, in which, in use, a layer of accreted ice is built up, wherein the target comprises a sample plate at the bottom of the well and an ice-engagement element positioned circumferentially around the sample plate and providing a side wall of the well; wherein the sample plate is rotatable relative to the ice-engagement element.

12. Ice accretion apparatus of claim 1, wherein the bottom unit is in the form of an ice adhesion test device that further comprises: torque means for applying a rotational torque between the sample plate and the ice-engagement element to try, in use, to rotate the sample plate relative to the ice-engagement element against the resistance of the layer of accreted ice; and transducer means for measuring the rotational torque.

13. Ice accretion apparatus of claim 12, wherein the ice-engagement element has an inner peripheral wall which has recesses for keying with the layer of accreted ice to prevent rotation of the layer of accreted ice relative to the ice-engagement element.

14. Ice accretion apparatus of claim 1, wherein the bottom unit is in the form of a runback ice test device.

15. Ice accretion apparatus of claim 14, wherein the target comprises a platform having an upper face which is separated into a first section and a second section by a protruding thermal barrier.

16. Ice accretion apparatus of claim 15, wherein the runback ice test device further comprises at least one of
platform inclination means arranged to incline the platform such that the second section is above the first section; and
first heater means for producing localised heating of the first section of the platform for keeping the first section of the platform substantially free of accreted ice as a layer of accreted ice is, in use, built up on the second section of the platform.

17. Ice accretion apparatus of claim 16, wherein the runback ice test device further comprises second heater means for producing localised heating of the second section of the platform, wherein the second heater means for producing localised heating of the second section of the platform is further for producing, when the platform is inclined, runback of melted ice from the layer of accreted ice and over the barrier and onto the first, lower section of the platform, and wherein the ice accretion apparatus further comprises a heater means controller for independently switching on and off the first and second heater means.

18. An ice accretion system comprising:
a column having a longitudinal axis, a side wall, and a central chamber having top and bottom ends, wherein the side wall comprises a plurality of tubular segments and wherein the tubular segments are releasably stacked on top of one another;
a top unit which closes the top end of the chamber and is arranged to receive a droplet discharge device for producing water droplets;
a first droplet discharge device arranged to be fitted to the top unit and comprising at least one nozzle having a first diameter that at least partially determines a diameter of at least one water droplet formed by the at least one nozzle having the first diameter;
a second droplet discharge device arranged to be fitted to the top unit and comprising at least one nozzle having a second diameter that at least partially determines a diameter of at least one water droplet formed by the at least one nozzle having the second diameter, the second diameter different from the first diameter;
a bottom unit which closes the bottom end of the chamber and includes a target; and
chamber cooling means configured to cool the chamber during a test and thereby to cool water droplets produced by the first or second droplet discharge device, whereby, in use during the test, a layer of accreted ice is built up on the target.

19. Ice formation apparatus comprising: a column having an annular side wall defining a chamber which has a top end and a bottom end, wherein the annular side wall of the column has a wall cavity with an inlet and an outlet for a cooling fluid for cooling the chamber and comprises a plurality of tubular segments wherein the tubular segments are releasably stacked on top of one another; a droplet discharging device for producing water droplets at the top end of the chamber; and a target at the bottom end of the chamber on which, in use, a layer of accreted ice is built up from the water droplets.

* * * * *